United States Patent
Zhong et al.

(10) Patent No.: US 7,869,030 B2
(45) Date of Patent: Jan. 11, 2011

(54) AGGREGATES OF PLURAL TRANSITION METAL NANOPARTICLES AND PLURAL CYANINE DYE MOLECULES

(75) Inventors: Chuan-Jian Zhong, Endwell, NY (US); Stephanie I-Im Lim, Vestel, NY (US)

(73) Assignee: Research Foundation of State University of New York, Binghamton, NY (US)

( * ) Notice: Subject to any disclaimer, the term of this patent is extended or adjusted under 35 U.S.C. 154(b) by 356 days.

(21) Appl. No.: 11/961,809

(22) Filed: Dec. 20, 2007

(65) Prior Publication Data

US 2008/0316480 A1 Dec. 25, 2008

Related U.S. Application Data

(60) Provisional application No. 60/883,235, filed on Jan. 3, 2007.

(51) Int. Cl.
*G01J 3/44* (2006.01)
*G01N 21/64* (2006.01)
*G01N 21/65* (2006.01)

(52) U.S. Cl. .................. 356/301; 356/317; 356/445

(58) Field of Classification Search ............ 356/301
See application file for complete search history.

(56) References Cited

U.S. PATENT DOCUMENTS

| 6,586,787 | B1 | 7/2003 | Shih et al. |
| 6,818,117 | B2 | 11/2004 | Ferguson et al. |
| 2003/0198956 | A1 | 10/2003 | Makowski et al. |
| 2004/0086897 | A1 | 5/2004 | Mirkin et al. |
| 2004/0245209 | A1 | 12/2004 | Jung et al. |

OTHER PUBLICATIONS

Barazzouk et al., "Photoinduced Electron Transfer Between Chlorophyll a and Gold Nanoparticles," *J. Phys. Chem.* 109(2):716-23 (2005).

Chandrasekharan et al., "Dye-Capped Gold Nanoclusters: Photoinduced Morphological Changes in Gold/Rhodamine 6G Nanoassemblies," *J. Phys. Chem.* 104(47):11103-9 (2000).

Dulkeith et al., "Gold Nanoparticles Quench Fluorescence by Phase Induced Radiative Rate Suppression," *Nano Lett.* 5(4):585-9 (2005).

Ghosh et al., "Fluorescence Quenching of 1-methylaminopyrene Near Gold Nanoparticles: Size Regime Dependence of the Small Metallic Particles," *Chemical Physics Letters* 395:366-72 (2004).

Grabar et al., "Preparation and Characterization of Au Colloid Monolayers," *Anal. Chem.* 67(4):735-43 (1995).

Han et al., "Novel Interparticle Spatial Properties of Hydrogen-Bonding Mediated Nanoparticle Assembly," *Chem. Mater.* 15(1):29-37 (2003).

(Continued)

*Primary Examiner*—F. L Evans
(74) *Attorney, Agent, or Firm*—Nixon Peabody LLP

(57) ABSTRACT

The present invention is directed to an aggregate composed of a plurality of nanoparticles of a transition metal and a plurality of cyanine dye molecules that are interacting non-covalently. The nanoparticles are capped with a capping molecule, while the cyanine dye molecule can be cationic, anionic, or neutral cyanine dye. Methods of making such aggregates and for using them in detection of an analyte are also disclosed.

23 Claims, 32 Drawing Sheets

OTHER PUBLICATIONS

Hannah & Armitage, "DNA-Templated Assembly of Helical Cyanine Dye Aggregates: A Supramolecular Chain Polymerization," *Acc. Chem. Res.* 37(11):845-53 (2004).

Huang & Murray, "Quenching of $[Ru(bpy)_3]^{2+}$ Fluorescence by Binding to Au Nanoparticles," *Langmuir* 18(18):7077-81 (2002).

Israel et al., "Electroactivity of $Cu^{2+}$ at a Thin Film Assembly of Gold Nanoparticles Linked by 11-mercaptoundecanoic Acid," *Journal of Electroanalytical Chemistry* 517:69-76 (2001).

Kneipp et al., "Optical Probes for Biological Applications Based on Surface-Enhanced Raman Scattering from Indocyanine Green on Gold Nanoparticles," *Anal. Chem.* 77(8):2381-5 (2005).

Kometani et al., "Preparation and Optical Absorption Spectra of Dye-Coated Au, Ag, and Au/Ag Colloidal Nanoparticles in Aqueous Solutions and in Alternate Assemblies," *Langmuir* 17(3):578-80 (2001).

Leibowitz et al., "Structures and Properties of Nanoparticle Thin Films Formed via a One-Step Exchange—Cross-Linking—Precipitation Route," *Anal. Chem.* 71(22):5076-83 (1999).

Lian et al., "Ultrasensitive Detection of Biomolecules with Fluorescent Dye-doped Nanoparticles," *Analytical Biochemistry* 334:135-44 (2004).

Lim et al., "Absorption of Cyanine Dyes on Gold Nanoparticles and Formation of J-Aggregates in the Nanoparticle Assembly," *J. Phys. Chem.* 110(13):6673-82 (2006).

Lim et al., "Kinetic and Thermodynamic Assessments of the Mediator—Template Assembly of Nanoparticles," *J. Phys. Chem.* 109(7):2578-83 (2005).

Lim et al., "Multifunctional Fullerene-Mediated Assembly of Gold Nanoparticles," *Chem. Mater.* 17(26):6528-31 (2005).

Lu et al., "Surface-Enhanced Superquenching of Cyanine Dyes as J-Aggregates on Laponite Clay Nanoparticles," *Langmuir* 18(20):7706-13 (2002).

Maye et al., "Gold and Alloy Nanoparticles in Solution and Thin Film Assembly: Spectrophotometric Determination of Molar Absorptivity," *Analytica Chimica Acta* 496:17-27 (2003).

Templeton et al., "Redox and Fluorophore Functionalization of Water-Soluble, Tiopronin-Protected Gold Clusters," *J. Am. Chem. Soc.* 121(30):7081-9 (1999).

Thomas & Kamat, "Chromophore-Functionalized Gold Nanoparticles," *Acc. Chem. Res.* 36(12):888-98 (2003).

Wang et al., "DNA Binding of an Ethidium Intercalator Attached to a Monolayer-Protected Gold Cluster," *Anal. Chem.* 74(17):4320-7 (2002).

Wiederrecht et al., "Coherent Coupling of Molecular Excitons to Electronic Polarizations of Noble Metal Nanoparticles," *Nano Lett.* 4(11):2121-5 (2004).

Zamborini et al., "Electron Hopping Conductivity and Vapor Sensing Properties of Flexible Network Polymer Films of Metal Nanoparticles," *J. Am. Chem. Soc.* 124(30):8958-64 (2002).

Zhang et al., "Colorimetric Detection of Thiol-containing Amino Acids Using Gold Nanoparticles," *Analyst* 127:462-5 (2002).

Zheng et al., "Imparting Biomimetic Ion-Gating Recognition Properties to Electrodes with a Hydrogen-Bonding Structures Core—Shell Nanoparticle Network," *Anal. Chem.* 72(10):2190-9 (2000).

(1)

(2)

(3)

(4)

AGGREGATES OF PLURAL TRANSITION METAL NANOPARTICLES AND PLURAL CYANINE DYE MOLECULES

The present invention claims benefit of U.S. Provisional Application Ser. No. 60/883,235, filed Jan. 3, 2007, which is hereby incorporated by reference in its entirety.

This invention was made with government support under grant number CHE 0349040 awarded by National Science Foundation. The government has certain rights in this invention.

FIELD OF THE INVENTION

The present invention relates to aggregates of plural transition metal nanoparticles and plural cyanine dye molecules.

BACKGROUND OF THE INVENTION

The assembly of nanoparticles with controllable sizes, shapes, and interparticle properties is essential to the exploitation of the unique electronic, optical, magnetic, and chemical properties of the nanoscale materials. A challenging area in the exploitation of the optical properties of the dye-nanoparticle combination as spectroscopic probes, photochemical or sensory devices is the ability of controlling the inter-particle interactions and reactivities. In recent years, the coupling of molecularly-capped nanocrystals to molecular mediation has attracted increasing interest in developing such abilities. The capping/mediator molecules act as a protective shell, resisting the propensity of aggregation, and can also be tailored to define the interfacial spacing and chemistry in controllable ways. Many examples that exploit such nanostructured interfacial properties have recently emerged, including ligand-exchange reaction (see Hostetler, M. J., et al., *J. Am. Chem. Soc.* 118: 4212 (1996); Hostetler, M. J., et al., *Langmuir* 15: 3782 (1999); Templeton, A. C., et al., *J. Am. Chem. Soc.* 120: 1906 (1998); Templeton, A. C., et al., *J. Am. Chem. Soc.* 120: 4845 (1998)), layer-by-layer stepwise assembly (see Musick, M. D., et al., *Langmuir* 15: 844 (1999); Zamborini, F. P., et al., *J. Am. Chem. Soc.* 122: 4514 (2000); Templeton, A. C., et al., *Langmuir* 16: 6682 (2000)), DNA-linked assembly (see Mirkin, C. A., et al., *Nature* 382: 607 (1996); Elghanian, R., et al., *Science* 277: 1078 (1997); Taton, T. A., et al., *J. Am. Chem. Soc.* 122: 6305 (2000)), polymer- or dendrimer-mediated molecular recognition (see Boal, A. K., et al., *Nature* 404: 746 (2000); Boal, A. K., et al., *J. Am. Chem. Soc.* 124: 5019 (2002); Frankamp, B. L., et al., *J. Am. Chem. Soc.* 124: 15146 (2002); Srivastava, S., et al., *Chem. Mater.* 17: 487 (2005); Kariuki, N. N., et al., *Langmuir* 18: 8255 (2002)), molecularly-mediated exchange-crosslinking (see Leibowitz, F. L., et al., *Anal. Chem.* 71: 5076 (1999); Zheng, W. X., et al., *Anal. Chem.* 72: 2190 (2000); Han, L., et al., *Chem. Mater.* 15: 29 (2003)), and multidentate thioether-mediated assembly (see Maye, M. M., et al., *J. Phys. Chem. B* 109: 2578 (2005)). Emerging applications of the molecularly-mediated assemblies of nanoparticles include chemical sensing (see Zheng, W. X., et al., *Anal. Chem.* 72: 2190 (2000); Han, L., et al., *Anal. Chem.* 73: 4441 (2001); Zamborini, F. P., et al., *J. Am. Chem. Soc.* 124: 8958 (2002); Leopold, M. C., et al., *Faraday Discuss.* 125: 63 (2004); Israel, L. B., et al., *J. Electroanal. Chem.* 517: 69 (2001)), catalysis (see Narayanan, R., et al., *J. Am. Chem. Soc.* 126: 7194 (2004); Zhong, C. J., et al., in *Nanotechnology in Catalysis*, Zhou, B., et al., Eds.; Kluwer Academic/Plenum Publishers: New York, Vol. 1, Chapter 11, pp 222-248 (2004); Zhong, C. J., et al., *Adv. Mater.* 13: 1507 (2001)), drug delivery, nanoelectronics (see Musick, M. D., et al., *Langmuir* 15: 844 (1999); Chen, S. *Langmuir* 17: 6664 (2001); Chen, S., *J. Am. Chem. Soc,* 122: 7420 (2000); Chen, S., et al., *Am. Chem. Soc.* 124: 5280 (2002); Hicks, J. F., et al., *J. Am. Chem. Soc.* 123: 7048 (2001)), and medical diagnostics (see Mirkin, C. A., et al., *Nature* 382: 607 (1996); Elghanian, R., et al., *Science* 277: 1078 (1997); Taton, T. A., et al., *J. Am. Chem. Soc.* 122: 6305 (2000); Zheng, W. X., et al., *Analyst* 125: 17 (2000)). The immobilization of dye molecules onto nanoparticles has on the other hand attracted recent interest in exploiting the optical properties for applications in chemical and biological systems. For example, the fluorescence quenching of small dye molecules has been studied using gold nanoparticles of different sizes (see Huang, T., et al., *Langmuir* 18: 7077 (2002); Ghosh, S. K., et al., *Chem. Phys. Lett.* 395: 366 (2004)). It is revealed that complementary oligonucleotides lead to the quenching phenomenon for single stranded DNA linked-metal nanoparticles (see Li, H., et al., *J. Am. Chem. Soc.* 126: 10958 (2004); Li, H., et al., *Anal. Chem.* 76: 5414 (2004)), which eliminates target labeling. DNA hybridization assay has been demonstrated using bar-coded metal nanowires with selected fluorophores that have wavelength-dependent reflectivities (see Nicewarner-Pena, S. R., et al., *Science* 294: 137 (2001); Nicewarner-Pena, S. R., et al., *J. Phys. Chem., B* 107: 7360 (2003)). Oligonucleotides that contains single base mismatch are recently shown to be effectively distinguished based on the quenching properties of gold nanoparticles on fluorescence dyes (see Maxwell, D. J., et al., *J. Am. Chem. Soc.* 124: 9606 (2002)). The use of fluorescent dye-doped nanoparticles for bioanalytical detection has shown to be useful in medical diagnostics and labeling (see Lian, W., et al., *Anal. Biochem.* 334: 135 (2004)). The study of dye-capped metal nanoparticles has also attracted interest in the basic research (see Thomas, K. G., et al., *Acc. Chem. Res.* 36: 888 (2003); Chandrasekharan, N., et al., *J. Phys. Chem. B* 104; 11103 (2000); Barazzouk, S., et al., *J. Phys. Chem. B* 109: 716 (2005); Nasr, C. P., et al., *J. Phys. Chew.* 100: 11054 (1996); Cu, T., et al., *Chem. Mater.* 15: 1358 (2003); Hranisavljevic, J., et al., *J. Am. Chem. Soc.* 124: 4536 (2002); Wang, G. L., et al., *Anal. Chem.* 74: 4320 (2002); Huang, T., et al., *J. Phys. Chem. B* 105: 12498 (2001); Templeton, A. C., et al., *J. Am. Chem. Soc,* 121: 7081 (1999); Dulkeith, E., et al., *Nano Lett.,* 5: 585 (2005)). In the study of the fluorescence quenching as a result of the proximity of dye molecules to the metal nanoparticle surface, important insights have been gained into the molecular interactions involving electron or energy transfer between dye and metal particles (see Thomas, K. G., et al., *Acc. Chew. Res.* 36: 888 (2003)). While the prior studies have shown promising application of dye-nanoparticle combination as spectroscopic probes, relatively little attention has been paid to how the interparticle interactions and reactivities can be utilized for nanostructured assembly.

The present invention is directed to overcoming these deficiencies in the art.

SUMMARY OF THE INVENTION

One aspect of the present invention is directed to a method of forming aggregates of nanoparticles and dyes by providing nanoparticles of a transition metal and providing cyanine dye molecules. The nanoparticles are capped with a positive or negative capping group, while the cyanine dye molecules can be cationic, anionic, or neutral cyanine dye molecules. The nanoparticles and the cyanine dye molecules are contacted under conditions effective to form aggregates of a plurality of the nanoparticles and a plurality of the dye molecules, with the nanoparticles and cyanine dye molecules interacting non-covalently.

Another aspect of the present invention is directed to an aggregate of a plurality of nanoparticles of a transition metal and a plurality of cyanine dye molecules, where the nanoparticles and cyanine dye molecules interact non-covalently. The nanoparticles are capped with a positive or negative capping group, while the cyanine dye molecules can be cationic, anionic, or neutral cyanine dyes.

A further aspect of the present invention is directed to a method of assembling aggregates of gold nanoparticles. This involves providing capped gold nanoparticles and providing cyanine dye molecules. The nanoparticles are capped with a positive or negative capping molecule, while the cyanine dye molecules can be cationic, anionic, or neutral cyanine dyes. The capped gold nanoparticles and the cyanine dye molecules are contacted under conditions effective to form aggregates of a plurality of the gold nanoparticles and a plurality of the cyanine dye molecules. The cyanine dye molecules and the gold nanoparticles form J-aggregates and may undergo hydrophobic interaction.

The present invention is also directed to a method of detecting an analyte in a sample. This method involves providing a sample potentially containing the analyte and providing the aggregate of the present invention. The sample and the aggregate are contacted and a change in the aggregate caused by the analyte is detected. Detection of such changes permits detection of the analyte in the sample.

The spectroscopic properties of the nanoparticle-dye combinations, in accordance with the present invention, provide benefits in spectroscopic detection via signals from, e.g., surface plasmon resonance band shift (red shift), fluorescence quenching (quantitative quenching and releasing), and surface enhanced Raman scattering (SERS, remarkable signal enhancement in solution). Some of the uses include: spectroscopic labels, chemical sensors, photochemical devices, and photoexcited fluorophore pathways.

Nanoparticle-dye combinations can be used as spectroscopic labels. For example, a fluorescence label on such a combination can be used for DNA-binding detection, antibody/antigen detection, or to Bio-bar code metal nanowires for multiplex bioanalysis. Additionally, a fluorecence label could act as a SERS label oil a nanoparticle-dye combination in a bioassay of DNA or protein binding, or as a nanobiotransducer.

Nanoparticle-dye combinations can also be used as chemical sensors. Chemical detection of, for example, chemical vapors, can be accomplished by electronic coupling. Other methods of detection include optical colorimetric changes and electrical conductivity changes.

Another use of nanoparticle-dye combinations is in photochemical devices such as photosensitizers on nanoparticles (especially when supported on $TiO_2$ nanoparticles, ZnO, $SnO_2$, $Nb_2O_5$), and photochemical sensors.

Nanoparticle-dye combinations can also be utilized as photoexcited fluorophore pathways. Energy transfer to nanoparticles, electron transfers to nanoparticles, and intermolecular/intramolecular interaction between the nanoparticles and dyes can be measured, as can constructive and destructive interference resulting from polarization coupling.

BRIEF DESCRIPTION OF THE DRAWINGS

FIG. 2A shows how the surface plasmon (SP) absorbance band shifts as the nanoparticles and dyes aggregate and react to the presence of analyte (see FIG. 2B).

FIG. 3A shows how the fluorescence of the fluorescent dye is quenched as the nanoparticles and dyes aggregate. As analyte exchanges places with the dye, the fluorescence emission is restored (see FIG. 3B).

FIG. 4A shows how the surface enhanced Raman spectroscopy (SERS) absorbance band shifts as the nanoparticles and dyes aggregate and react to the presence of analyte (see FIG. 4B).

FIG. 10A shows the spectra for different concentrations of the ICD. [ICD]=0.03, 0.07, 0.10, 0.13, 0.17, 0.20, 0.23, and 0.27 µM. FIG. 10B shows a graph plotting the peak intensity at 1281 $cm^{-1}$ vs. concentration of the dye. [ICD]=0.03, 0.07, 0.10, 0.13, 0.17, 0.20, 0.23, and 0.27 µM.

(FIG. 13A) pH=3, (FIG. 13B) pH=43 (FIG. 13C) pH=5, and (FIG. 13D) pH=10. [ICD]=0.33 µM.

FIG. 19A shows solid curves for spectral evolution of the π-π* bands and J-band of the dyes upon addition of $Au_{nm}$ into the solution of ICD ([$Au_{nm}$]=0.42 nM and [ICD]=9.8 μM) and dashed curves for the change of the SP-band of Au nanoparticles upon addition of ICD into the solution of $Au_{nm}$ ([$Au_{nm}$]=0.42 nM and [ICD]=0.64 μM) (only the first and the last spectra are show). The arrow indicates the direction of the spectral evolution within the time frame of 20 min. FIG. 19B shows the comparison of the π-π* bands and J-band of the dyes in solutions upon adding different concentrations of Au nanoparticles, [$Au_{nm}$]=0 (dashed line), 0.17 (a), 0.42 (b), and 1.5 nM (c). ([ICD]=9.6 μM). The spectra were recorded within 10 sec.

FIGS. 20A and 20B show [$Au_{nm}$]=2.0 nM with different concentrations of dye, [ICD]=0.16 (FIG. 20A) and 0.33 μM (FIG. 20B) (with 0.2% ethanol). FIGS. 20C and 20D show [ICD]=0.17 μM (with 3% ethanol) with different concentrations of $Au_{nm}$, [$Au_{nm}$]=4.0 (FIG. 20C) and=2.7 nM (FIG. 20D). Curves (a) are for $Au_{nm}$ before adding ICD and curves (b) are for $Au_{nm}$ upon addition of ICD (the arrow indicates the direction of the spectral evolution within the time frame of 45 min).

FIG. 22B is with [$Au_{nm}$]=4.0 nM and [ICD]=0.17 μM.

DETAILED DESCRIPTION OF THE INVENTION

One aspect of the present invention is directed to a method of forming aggregates of nanoparticles and dyes by providing nanoparticles of a transition metal and providing cyanine dye molecules. The nanoparticles are capped with a positive or negative capping group, while the cyanine dye molecules can be cationic, anionic, or neutral cyanine dye molecules. The nanoparticles and the cyanine dye molecules are contacted under conditions effective to form aggregates of a plurality of the nanoparticles and a plurality of the dye molecules, with the nanoparticles and cyanine dye molecules interacting non-covalently.

Figure 1:
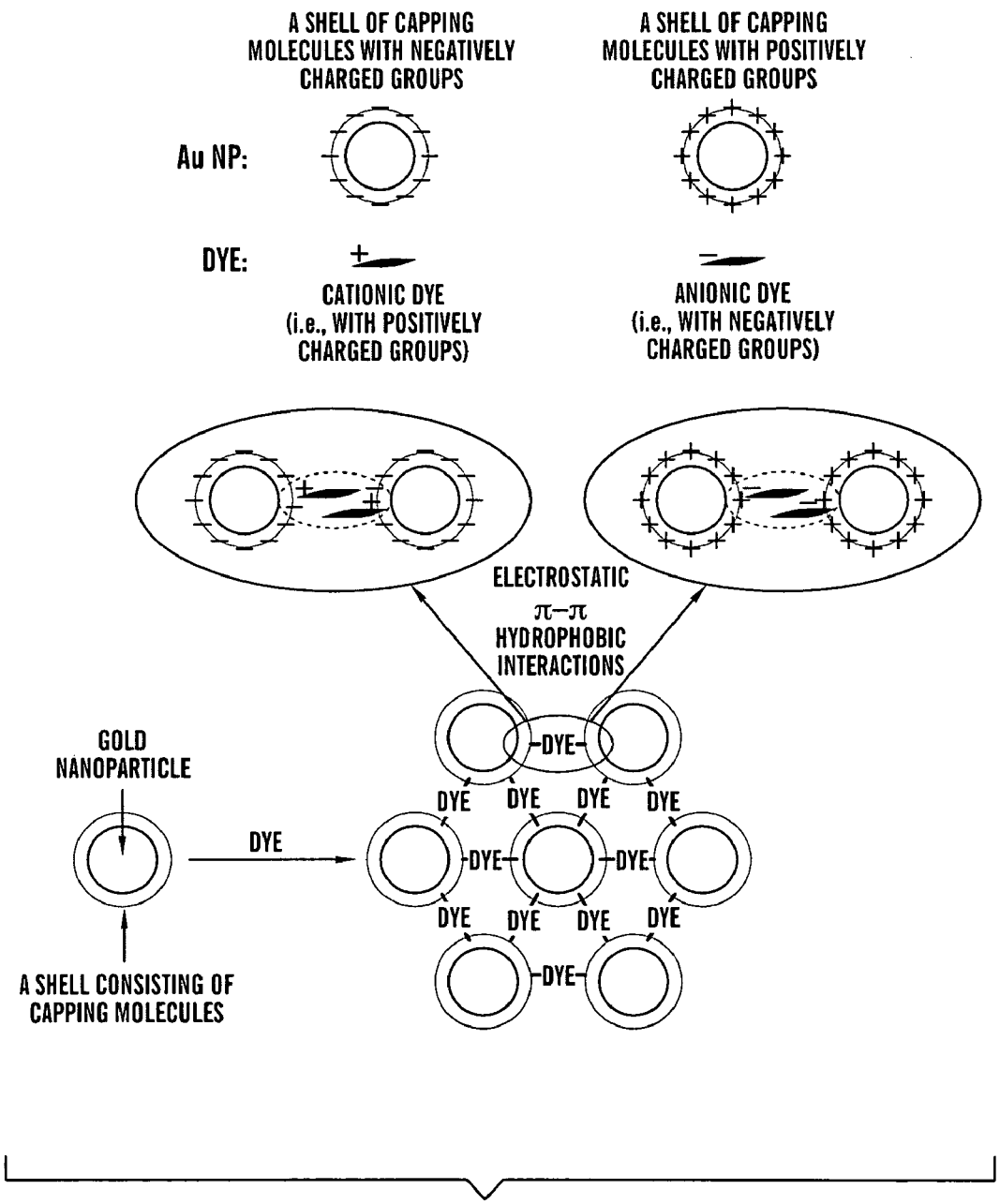
FIG. 1 shows the formation of an aggregate of capped gold nanoparticles and dye molecules.

FIG. 1 shows the formation of an aggregate of capped gold nanoparticles and dye molecules. As shown, gold nanoparticles having a shell consisting of positively or negatively charged capping molecules are contacted with either an anionic or cationic dye. Interactions between the nanoparticle capping molecules and the dye as well as between dyes allow for the formation of the aggregate.

Metals used in the nanoparticles of the present invention include copper, silver, gold, and mixtures thereof.

The cationic, anionic, and neutral cyanine dyes are described in Li, Q., et al., *Moleculies* 2: 91-98 (1997) or Hannah, K. C., et al., *Acc. Chem. Res*, 37; 845-853 (2004), which are hereby incorporated by reference in their entirety. See Table 1 for the structural formulae of examples of suitable cyanine dyes.

TABLE 1

ID #

Neutral Dyes

Dye 551077  N-1

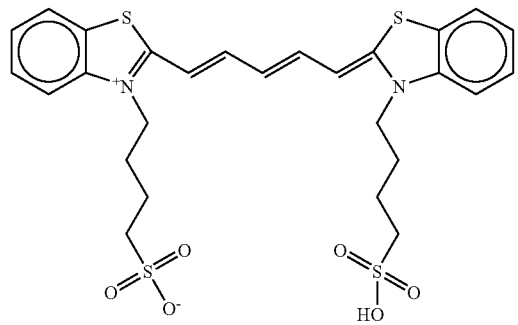

TABLE 1-continued
ID #
Dye 551428  N-2
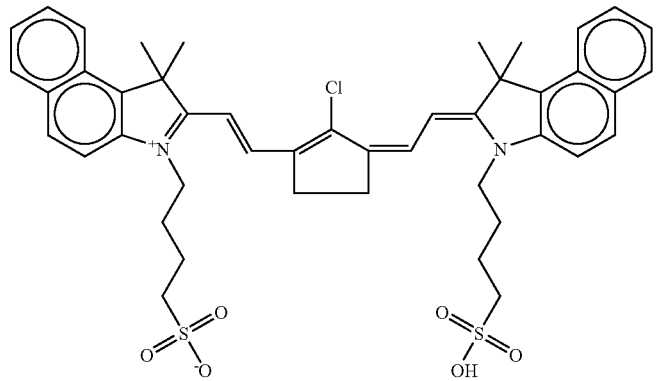
Anionic Dyes
Dye 551522  A-1
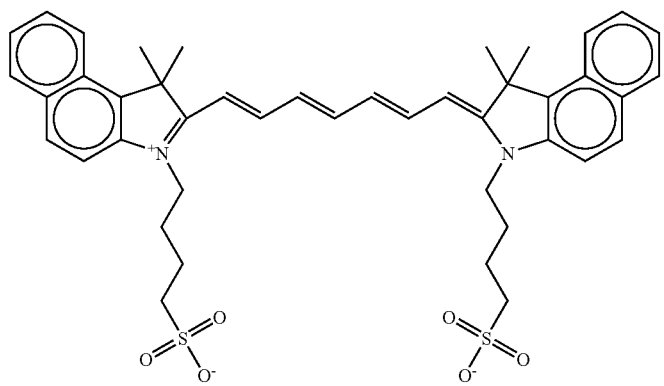
Dye 551266  A-2
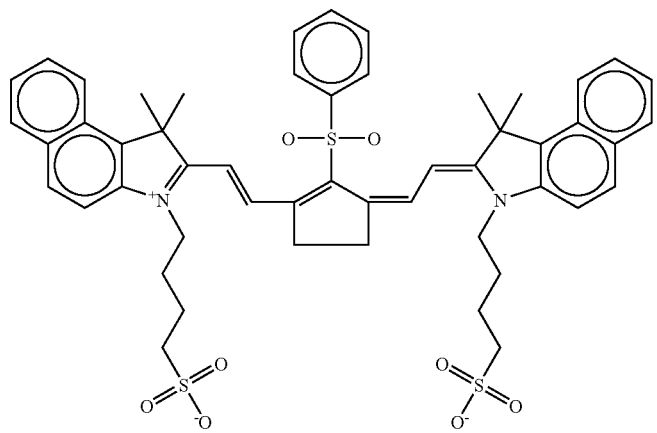
Cationic Dyes
Dye 551009  C-1
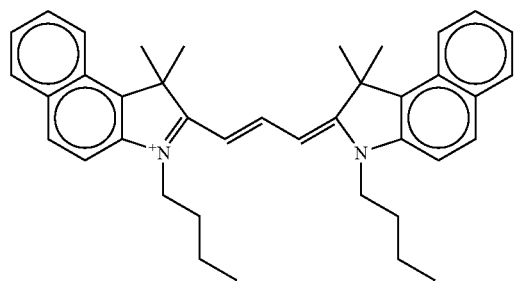

TABLE 1-continued
| ID # | | |
|---|---|---|
| Dye 551064 | C-2 | 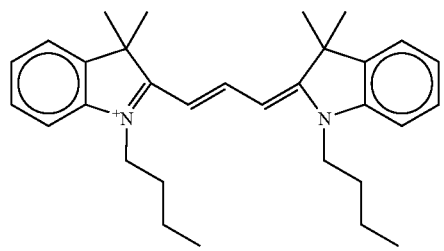 |
| Dye 551470 | C-3 | 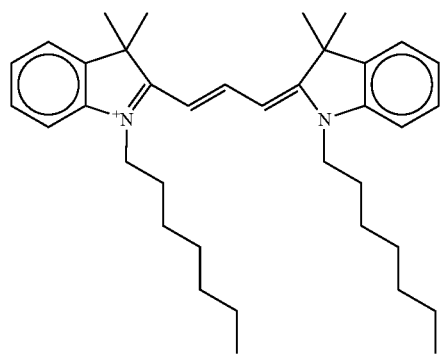 |
| Dye 551024 | C-4 | 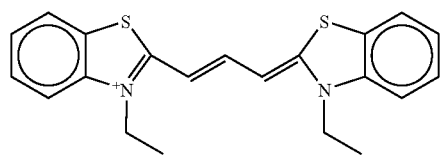 |
| Dye 551299 | C-5 | 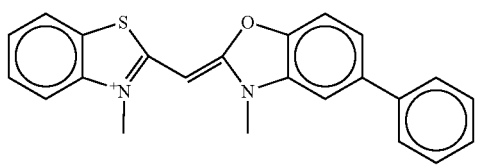 |
| Dye 551125 | C-6 | 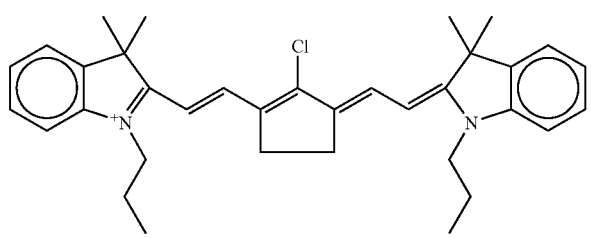 |
| Dye 551409 | C-7 | 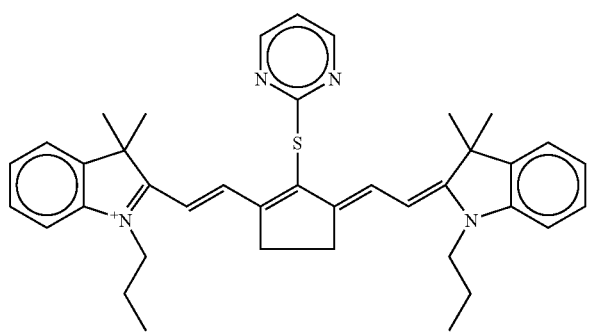 |

TABLE 1-continued

ID #

Dye 551518  C-8  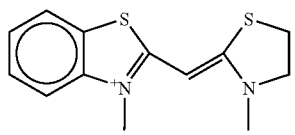

The aggregates formed can have diameters of 1-100 nanometers and may be J-aggregates. The aggregation may be caused by electrostatic interaction, hydrophobic interaction, and π-π interaction or other non-covalent interaction.

The understanding of interparticle interactions and reactivities of metal or semiconductor nanoparticles in the presence of chemical or biological species is a challenging area in the exploitation of the optical or electrical properties for spectroscopic nanoprobes, photochemical or sensory devices. Molecularly-organized aggregates such as J-aggregates are interesting because of their unique electronic and spectroscopic properties (Kobayashi, T., Ed., *J-Aggregates*, World Scientific Publishing Co.: Singapore (1996); Hannah, K. C., et al., *Acc. Chem. Res.* 37: 845 (2004), which are hereby incorporated by reference in their entirety). In J-aggregate, the 1-dimensional arrangement is such that the transition moments of monomers are aligned parallel to the line joining their centers in an end-to-end fashion. The most characteristic feature of J-aggregate is the red-shifted narrow absorption band (J-band) with respect to the monomer absorption. While the formation of J-aggregates are well known for cyanine dyes and a number of other dyes, the understanding of how such interactions are operative in the adsorption and assembly of nanoparticles is still limited (Kobayashi, T., Ed., *J-Aggregates*, World Scientific Publishing Co.; Singapore (1996); Hannah, K. C., et al., *Acc. Chem. Res.* 37; 845 (2004), which are hereby incorporated by reference in their entirety). In recent studies nanoparticles of synthetic clay or silica coated with cyanine dyes or polymers have been shown to form J-aggregated assemblies in water, exhibiting absorption characteristics corresponding to small J-aggregate domains and fluorescence superquenching characteristics (Lu, L. D., et al., *Langmitir* 18; 7706 (2002); Jones, R. M., et al., *Proceedings of the National Academy of Sciences of the United States of America* 98: 14769 (2001), which are hereby incorporated by reference in their entirety).

The nanoparticles may be capped by a negative or positive capping molecule. Suitable capping agents include acrylates, N,N-trimethyl(undecylmercapto)-ammonium, tetrabutylammonium tetrafluoroborate (TBA), tetramethylammonium bromide (TMA), cetyltrimethylammonium bromide (CTAB), citrates, poly methacrylate, ascorbic acid, DNAs, 2-mercaptopropionic acid (MPA), 3-mercaptopropionic acid (MPA), 11-mercaptoundecanoic acid (MUA), 10-mercaptodecane-1-sulfonic acid, 16-mercaptohexadecanoic acid, duimide, N-(2-mercaptopropionyl) glycine (tiopronin), 2-mercaptoethanol, 4-mercapto-1-butanol, dodecyl sulfate, amino acids, homocysteine, homocystine, cysteine, cystine, and glutathione.

Another aspect of the present invention is directed to an aggregate of a plurality of nanoparticles of a transition metal and a plurality of cyanine dye molecules, where the nanoparticles and cyanine dye molecules interact non-covalently. The nanoparticles are capped with a positive or negative capping group, while the cyanine dye molecules can be cationic, anionic, or neutral cyanine dyes.

The present invention is also directed to a method of detecting an analyte in a sample. This method involves providing a sample potentially containing the analyte and providing the aggregate of the present invention. The sample and the aggregate are contacted and a change in the aggregate caused by the analyte is detected. Detection of such changes permits detection of the analyte in the sample.

Figure 2A:
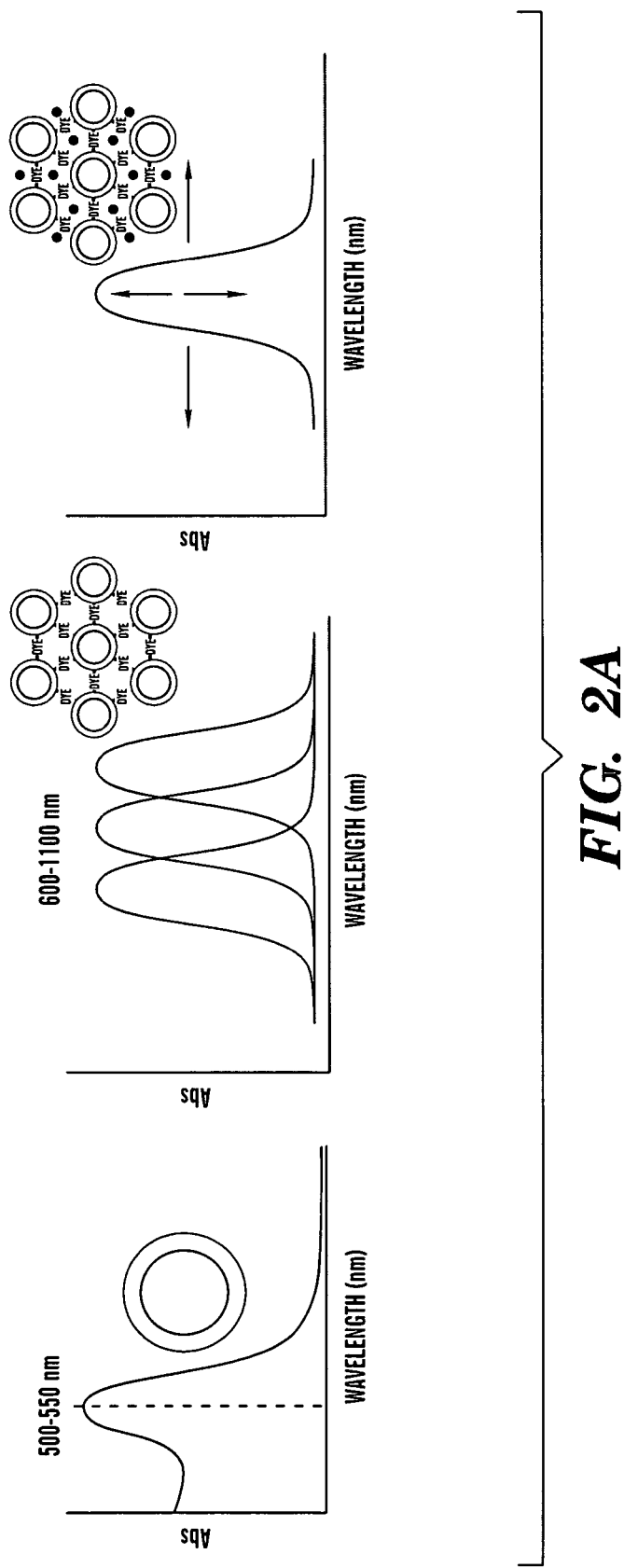
FIGS. 2A-B shows how the absorption properties of the nanoparticle-dye aggregates can be used to detect analyte.
Figure 2B:
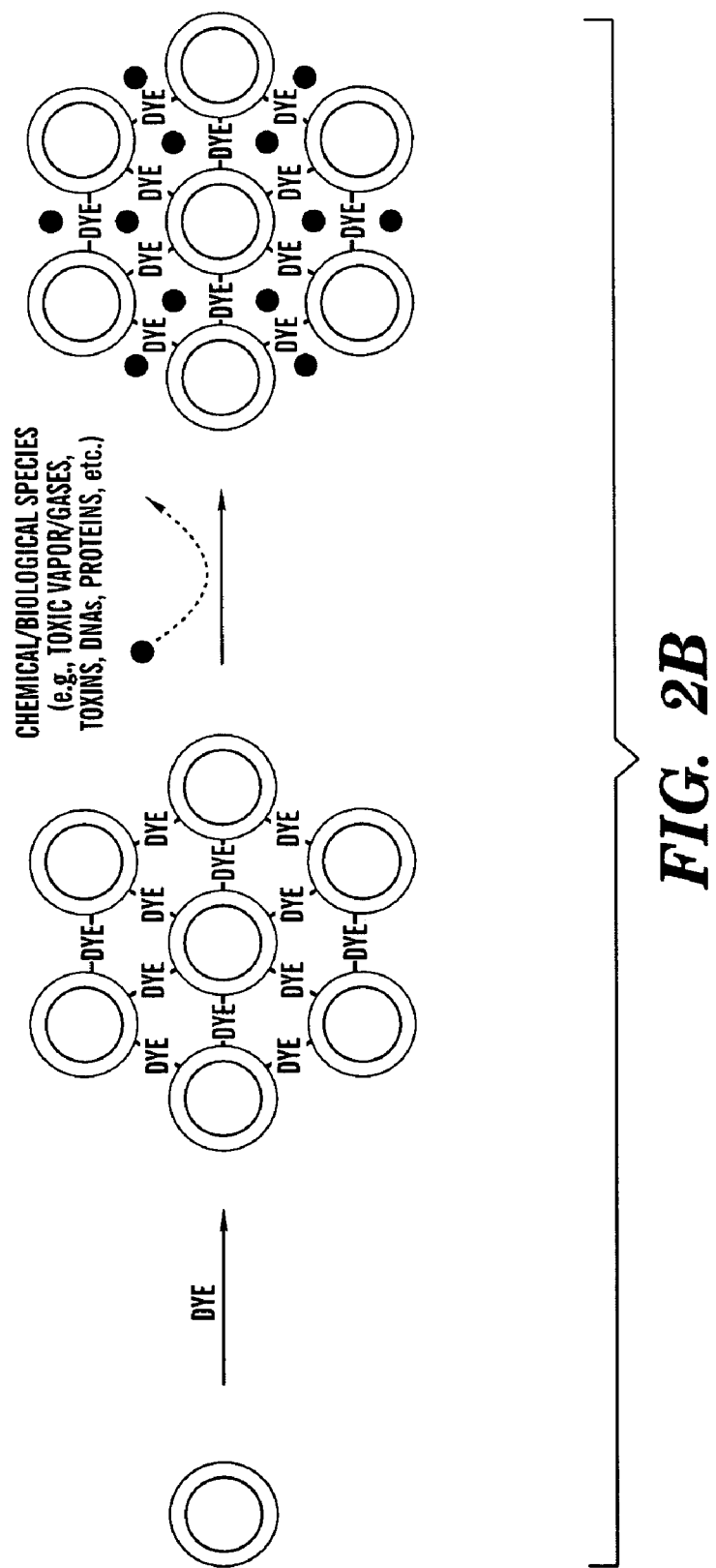

The assembly of the nanoparticle aggregates leads to a shift in the surface plasmon (SP) band wavelength. FIGS. 2A-B shows how the absorption properties of the nanoparticle-dye aggregates can be used to detect analyte. FIG. 2A shows how the SP absorbance band shifts as the nanoparticles and dyes aggregate and react to the presence of analyte (see FIG. 2B).

Figure 3A:
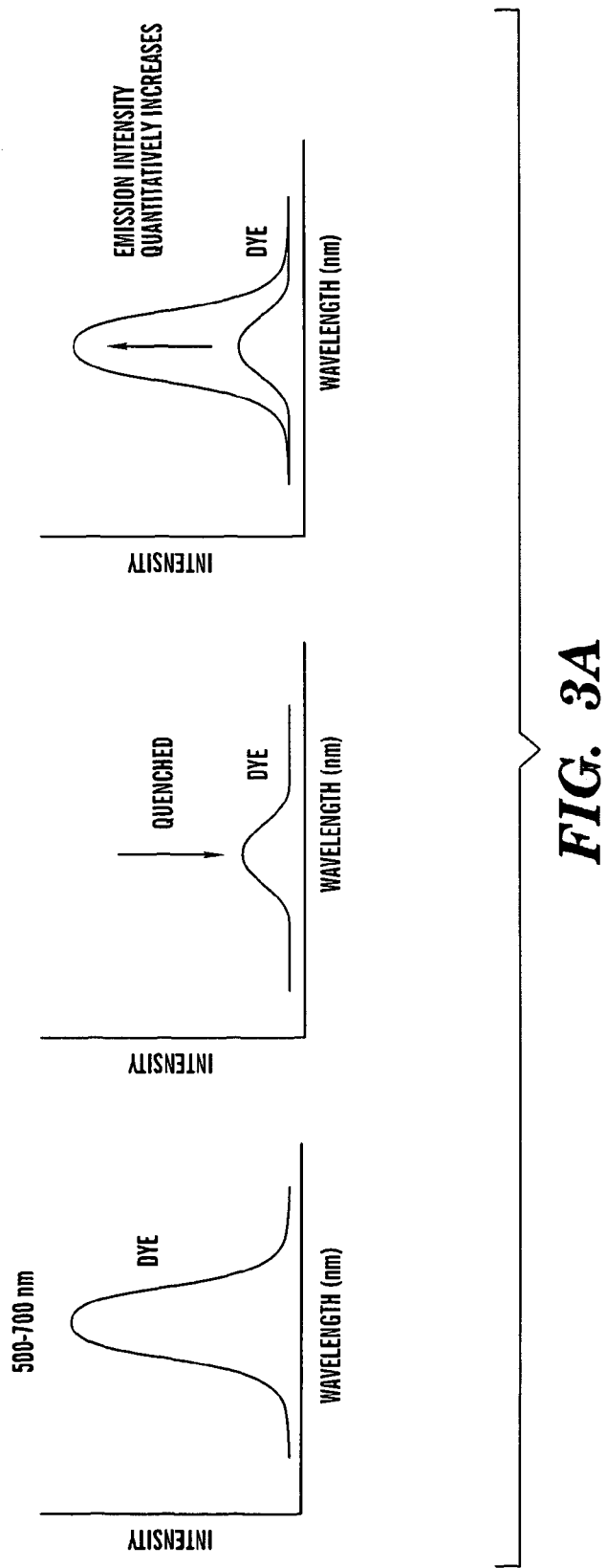
FIGS. 3A-B shows how the fluorescence emission properties of the nanoparticle-dye assemblies can be used to detect analyte.
Figure 3B:
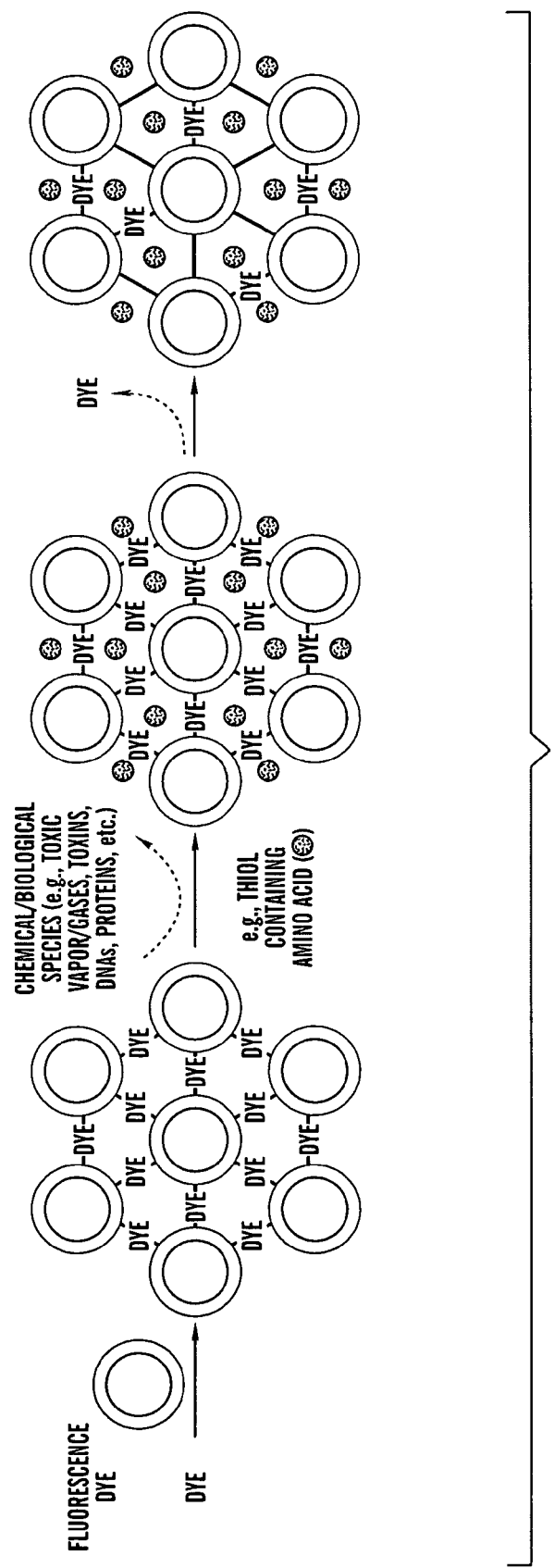

The emission intensity of fluorescent dye molecules is quenched when nanoparticles are added to the solution. FIGS. 3A-B shows how the fluorescence emission properties of the nanoparticle-dye assemblies can be used to detect analyte. FIG. 3A shows how the fluorescence of the fluorescent dye is quenched as the nanoparticles and dyes aggregate. An analyte can exchanges places with the dye. As the dye disassociated from the nanoparticle aggregate, the fluorescence emission is restored (see FIG. 3B).

Figure 4A:
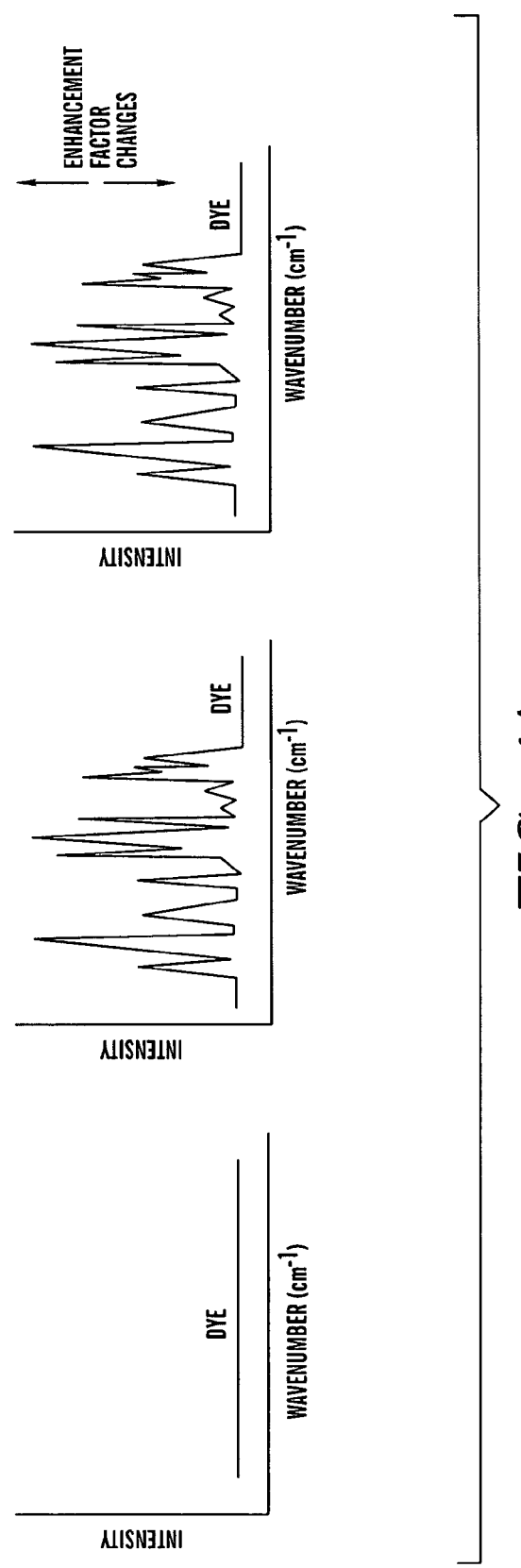
FIGS. 4A-B shows how the Raman spectroscopic properties of the nanoparticle-dye assemblies can be used to detect analyte.
Figure 4B:
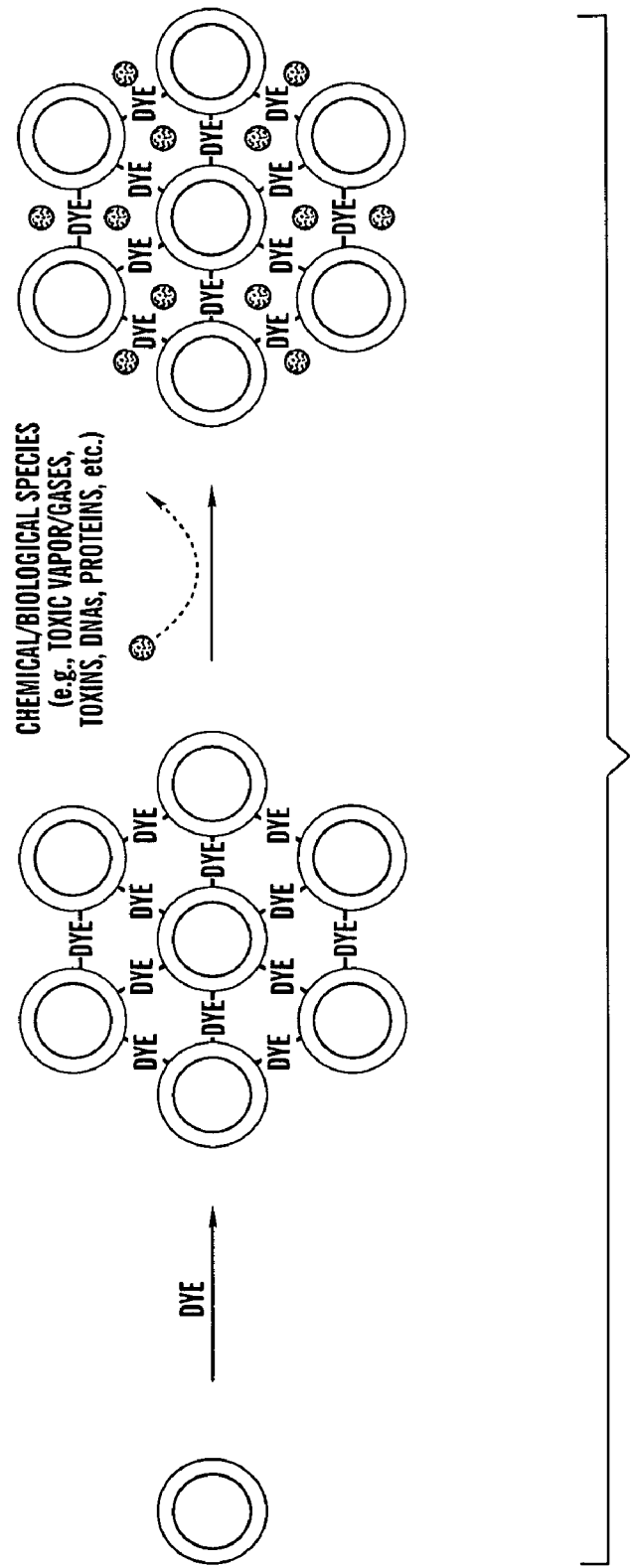

The adsorption of dyes on the nanoparticle surface results in a large signal enhancement in surface enhanced Raman spectroscopy (SERS) ($10^{3-12}$ times) due to surface enhancement by nanoparticle assemblies. FIGS. 4A-B shows how the Raman spectroscopic properties of the nanoparticle-dye assemblies can be used to detect analyte. FIG. 4A shows how the SERS absorbance band shifts as the nanoparicles and dyes aggregate and react to the presence of analyte (see FIG. 4B).

SERS has attracted much attention in recent studies. The quality of spectra obtained that have enhancement properties is of interest because of the small amounts of sample that is needed to be analyzed and the highly intense spectra that are obtained. In addition, Raman spectroscopy is highly interesting when it is used to analyze aqueous systems because the stretching modes of water are Raman inactive. This makes Raman complimentary to infrared spectroscopy where broad water peaks may interfere and obscure peaks of interest. To analyze gold or silver nanoparticles using Raman spectroscopy, it is necessary to deposit silver metal on surfaces or to electrochemically roughen the gold surface as well as using colloidal gold with co-adsorbed organic molecules (see Ni, J., et al., *Anal Chem*. 71: 4903 (1999), which is hereby incorporated by reference in its entirety). In one example, nanoparticles are used as nanoprobes to enhance the signal of added organic species. The nanoparticles act as a surface enhancement environment, where assembled molecules that are Raman active may benefit from an enhanced scattering signal.

EXAMPLES

Example 1

Chemicals

The chemicals included hydrogen tetracholoroaurate (HAuCl$_4$, 99%), sodium citrate (Cit, 99%), and ethanol (EtOH, 99.9%). All chemicals were purchased from Aldrich and used as received. Water was purified with a Millipore Milli-Q water system.

The cyanine dyes were obtained from Crysta-lyn Chemical Inc. Details for the synthesis of the dyes have been reported. See Li, Q., et al., *Molecules* 2; 91 (1997); Hamer, F. M., *The Cyanine Dyes and Related Compounds*, Wiley & Sons: New York, Vol. 18 (1964), which are hereby incorporated by reference in their entirety.

The synthesis of citrate-capped gold nanoparticles (Au$_{nm}$) followed the reported procedure (see Grabar, K. C., et al., *Anal. Chem.* 67: 735 (1995), which is hereby incorporated by reference in its entirety). Briefly, aqueous AuCl$_4^-$ (1 mM) was heated to boiling under vigorous stirring in a cleaned glass flask. At reflux, an excess (×3.8) of sodium citrate (38.8 mM stock solution) was quickly added into the solution. Citrate acts as both reducing and capping agents. The color of the solution turned from pale yellow to clear and to light red. This solution was allowed to react while stirring under reflux for 30 minutes, after which the heating mantle was removed and the solution was stirred under room temperature for another 3 hours. The particle size was determined using transmission electron microscopy.

Example 2

Measurements and Instrumentation

The dye mediated assembly of Au$_{nm}$ was carried out under ambient conditions. Briefly, upon adding a desired amount of dye solution (in ethanol) into aqueous solution of nanoparticles or vice versa, the solution was quickly mixed by purging for ~2 sec before the measurement of UV-Visible (UV-Vis) spectra. The spectra were collected over the range of 200-1100 nm with a HP 8453 spectrophotometer. A quartz cuvette with a path length of 1.0 cm was utilized. The stock concentration of gold nanoparticles was determined according to the absorbance data and the average size of the particles. As previously reported, the molar absorptivity ($\epsilon_{Au}$) for a 13-nm sized Au$_{nm}$ particles determined in aqueous solution at the surface plasmon resonance band maximum ($\lambda$=520 nm) was $2.01 \times 10^8$ M$^{-1}$·cm$^{-1}$. For ICD, the value of $\epsilon_{dye\ (ICD)}$ determined at $\lambda$=550 nm in aqueous solution was $1.15 \times 10^5$ M$^{-1}$ cm$^{-1}$. See Maye, M. M., et al., *Anal. Chemie. Acta.* 496: 17 (2003), which is hereby incorporated by reference in its entirety.

Fluorescence spectroscopy spectra were acquired with a SLM 48000 s Fluorometer with a MC320 monochromator. A fluorescence cuvette with a path length of 1.0 cm was utilized. The emission spectra were collected over a range of 550-700 nm. Excitation: 550 nm Emission: 608 nm, HV: 750-900.

FTIR spectra were acquired with a Nicolet Magna-IR 760 spectrometer with liquid Nitrogen cooled HgCdTe detector. The spectra were collected over the range of 400-4000 wavenumbers.

Example 3

SERS Spectra for ICD-Au$_{nm}$ Assembly

Figure 5A:
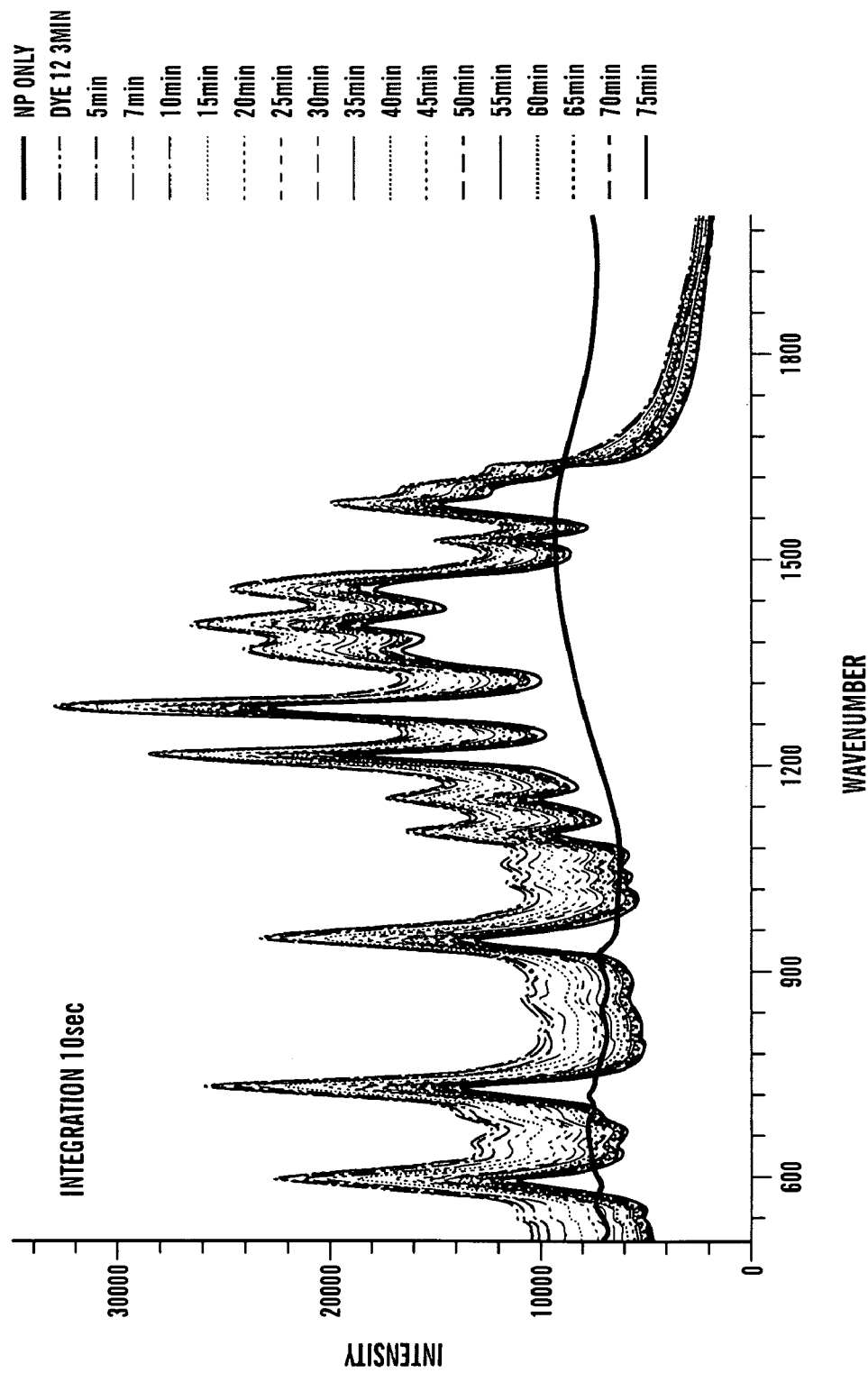
FIG. 5A shows SERS spectra of indolenine cyanine dye (ICD) upon addition of $Au_{nm}$. [ICD]=0.16 µM. Each spectrum was taken with an increment of 5 min over a time length of 80 mins.
Figure 5B:
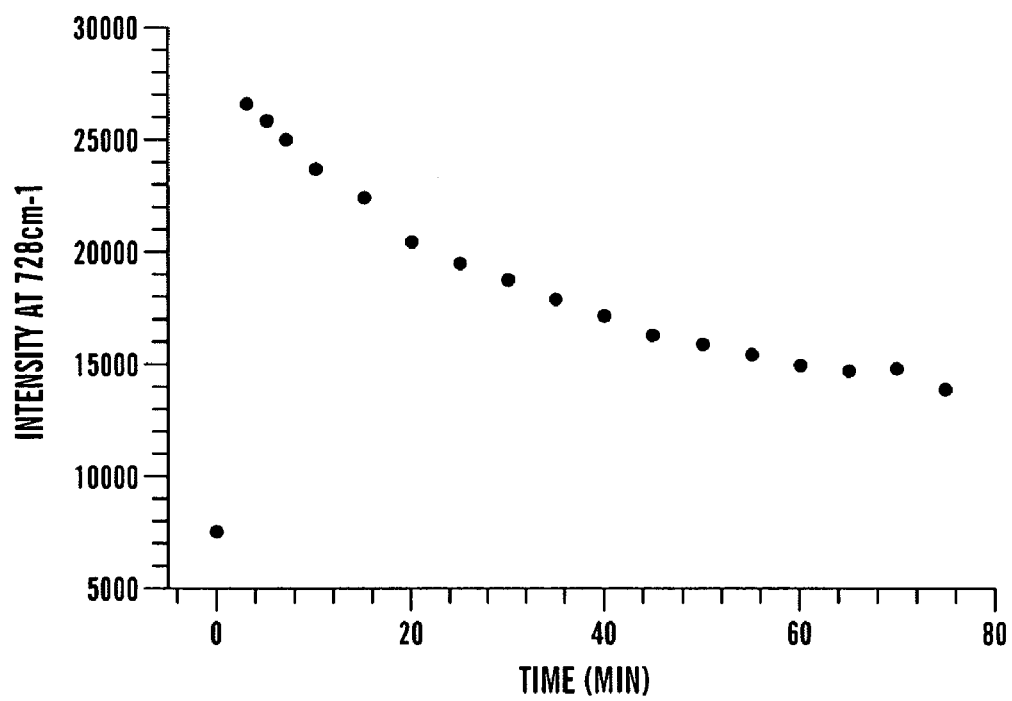
FIG. 5B shows a graph plotting intensity (I) at 728 $cm^{-1}$ vs. time.

The understanding of the surface interaction and stability of the ICD-Au$_{nm}$ assembly is studied using SERS. FIG. 5 represents a set of data obtained for the ICD-Au$_{nm}$ assembly as a function of time. As reported, the detection of dye molecules itself using SERS without any attachment to silver or gold nanoparticles is unfeasible. However, strong and distinct peaks are observed from the SERS spectrum when the dye molecules are attached to silver or gold nanoparticles. This allows it to act as a reporter molecule in a SERS optical probe. See Kneipp, J., et al., *Anal. Chem.* 77: 2381 (2005), which is hereby incorporated by reference in its entirety. Hence, upon the addition of Au$_{nm}$, the assembly solution was studied as a function of time (~80 min). An important finding in this experiment is that the intensity of the ICD mediated assembly of Au$_{nm}$ gradually decreases as time increase. This is due to the $\pi$-$\pi$ interaction of the dye assembly. The intensity eventually levels off after an hour. With this finding, most of the subsequent SERS spectra discussed below are taken within the time frame of 1 hour to ensure maximum intensity of the system is being recorded. This finding is different from that found using fluorescence spectroscopy. The fluorescence quenching of ICD occurs almost immediately (<1 min). See Lim, I-I. S., et al., *J. Phys. Chem. B*, 110: 6673 (2006), which is hereby incorporated by reference in its entirety. The rapid quenching is suggestive of a rapid adsorption of ICDs on Au$_{nm}$. The quenching is due to energy transfer as a result of the adsorption of ICD on Au$_{nm}$.

Example 4 pH Effect

As reported, cyanine dyes are fairly pH insensitive. FIG. 6 represents a set of experiments done for the mediated assembly of Au$_{nm}$ by ICD molecules when different pH of Au$_{nm}$ and ICD is explored by the addition of either HCl or NaOH.

Figure 6A:
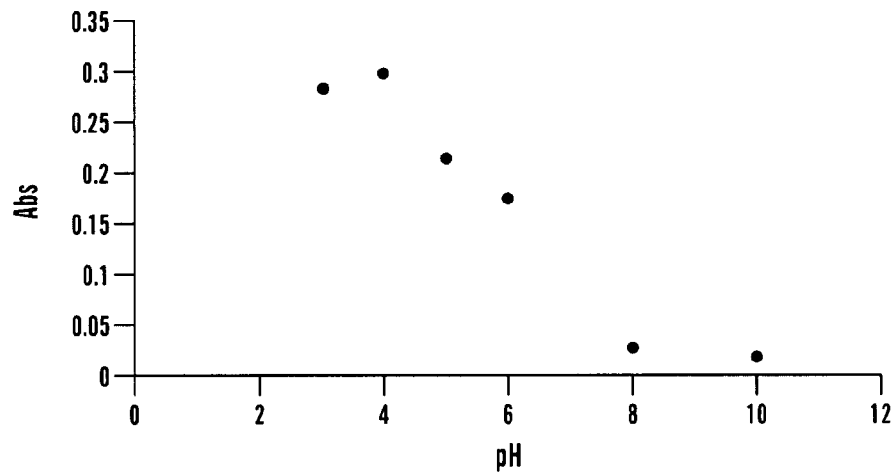
FIG. 6A shows a graph plotting absorbance (700 nm) vs. pH. The spectra were recorded within 30 min.
Figure 6B:
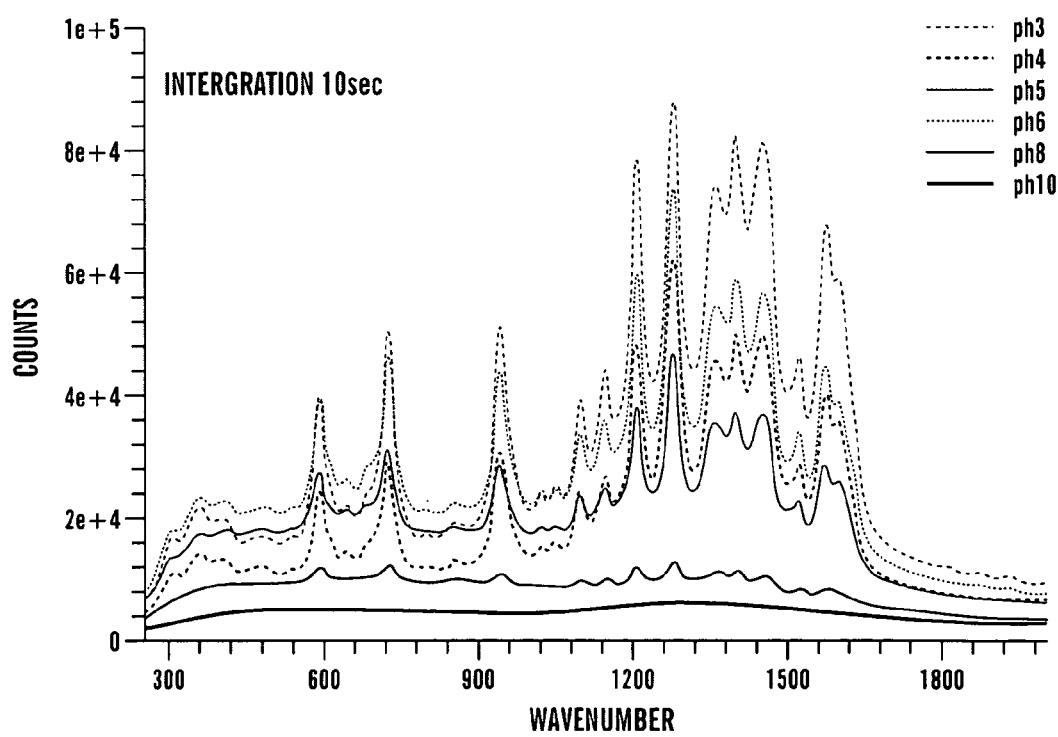
FIG. 6B shows SERS spectra for ICD-$Au_{nm}$ assembly.

When the pH of the Au$_{nm}$ and ICD solution is fairly low (i.e. a pH of 3-5), a spectral evolution is observed. The color for low ph solution turned from red to dark blue or dark purple within 1 minute and precipitation occurred within a day. At a higher pH (pH 8-10), the solution remained red and no spectral evolution was observed from the UV-Vis spectroscopy. As mentioned earlier, while ICD molecules are fairly pH insensitive, Au$_{nm}$ solution is highly dependent on the pH of the solution. The p$K_a$ values for citric are p$K_a$=3.1(a$_1$), 4.8 (a$_2$) and 6.4(a$_3$). As shown in FIG. 6A, the highest reactivity is observed when pH is around 4. This shows that the electrostatic interaction between the Au$_{nm}$ and ICD involved at least one of the deprotonated—CO$_2$H. At pH 3 and below, the Au$_{nm}$ start to aggregate due to instability while at a higher pH, no reactivity is observed due to complete deprotonation of the carboxylic acid groups.

The system is further studied using SERS. See FIG. 6B. The intensity observed did not represent any trend. One reason is due to the amount of ICD that was added. The average Au$_{nm}$ requires 170 ICD molecules for a complete monolayer coverage as determined by fluorescence quenching data. See Lim, I-I. S., et al., *J. Phys. Chem. B*, 110: 6673 (2006), which is hereby incorporated by reference in its entirety. In this case, ~180 ICD molecules were added. The addition of ICD molecules in solution will cause instability and fluctuation of the intensity as it is being recorded. Hence, they are not reliable.

Figure 7:
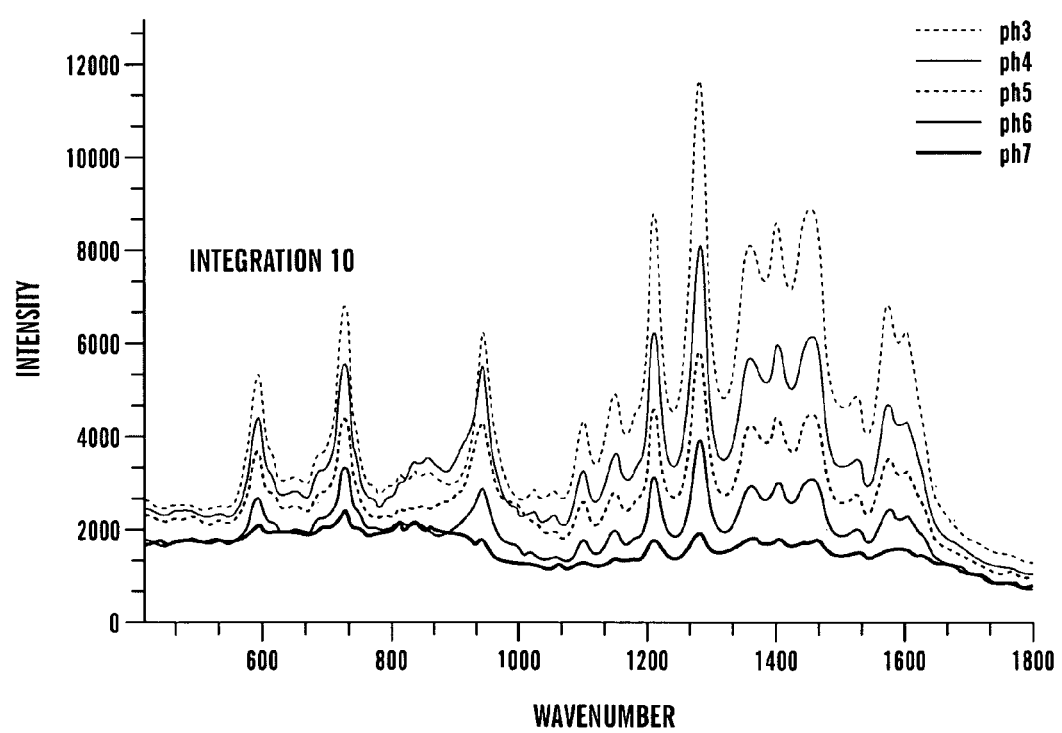
FIG. 7 shows SERS spectra of ICD-mediated assembly of $Au_{nm}$ in solutions at pH 3, 4, 5, 6, and 8. [ICD]=0.16 µM.

FIG. 7 represents another set of pH dependent study for the mediated assembly of $Au_{nm}$ when the concentration of ICD molecules is decreased and a sub-monolayer coverage of ICD molecules on the $Au_{nm}$ surface is expected.

Due to the low concentration ICD solution added, spectral evolution changes were not detected by UV-Vis spectroscopy. The color of each solution remained red for weeks without any sign of precipitation. However, when the system is examined using SERS, a trend is observed. See FIG. 7. At a low pH (pH 3), maximum intensity for all peaks was observed. The intensity started to decrease as the pH of the ICD-$Au_{nm}$ assembly solution increased. When the pH of the solution was increased to pH 8 barely any signals were detected.

Example 5

Homocysteine-Induced Disassembly and Re-Assembly

The tunability of the nanoparticle network structure is further studied. Because thiol has a strong binding affinity to gold surface, the exchange reaction of thiol with citrate could lead to disassembly of the network structure of ICD-$Au_{nm}$ assembly and, consequently, to the release of the ICD dye molecules from the gold surface back into the solution. While this idea seemed ideal, a previous study using UV-Vis spectroscopy failed to show the disassembly of ICD-Aun, assembly. One reason is the inability of UJV-V is to detect any small surface changes. However, use of SERS and fluorescence spectroscopy has demonstrated the viability of disassembling the ICD-$Au_{nm}$ assembly by introducing a thiol molecule—homocysteine (Hcys).

Figure 8A:
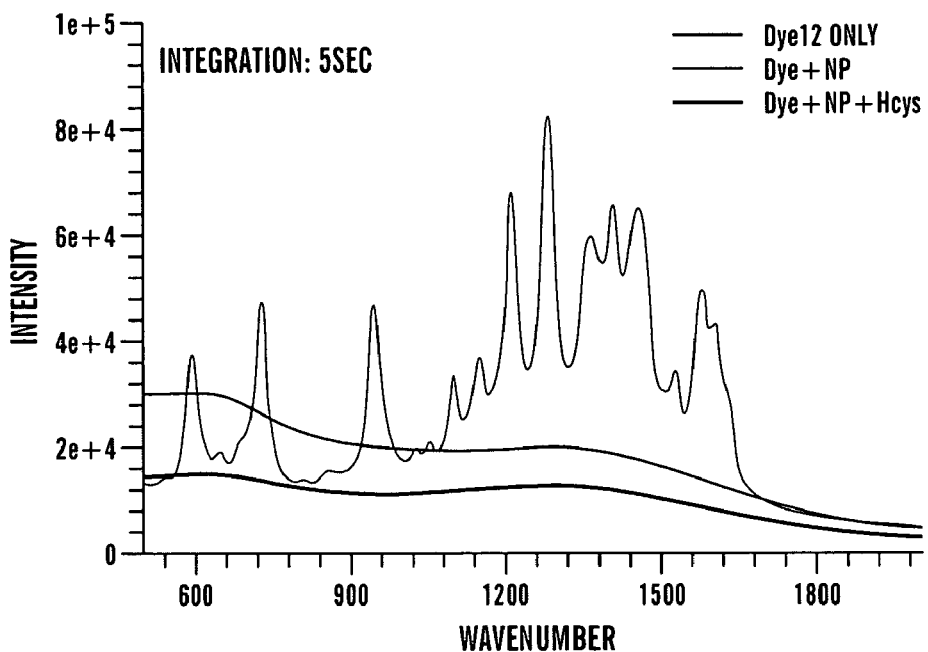
FIG. 8A shows SERS spectra for the solution of ICD-$Au_{nm}$ assembly upon addition of Hcys. [ICD]=0.8 µM, [cys]=80 µM.
Figure 8B:
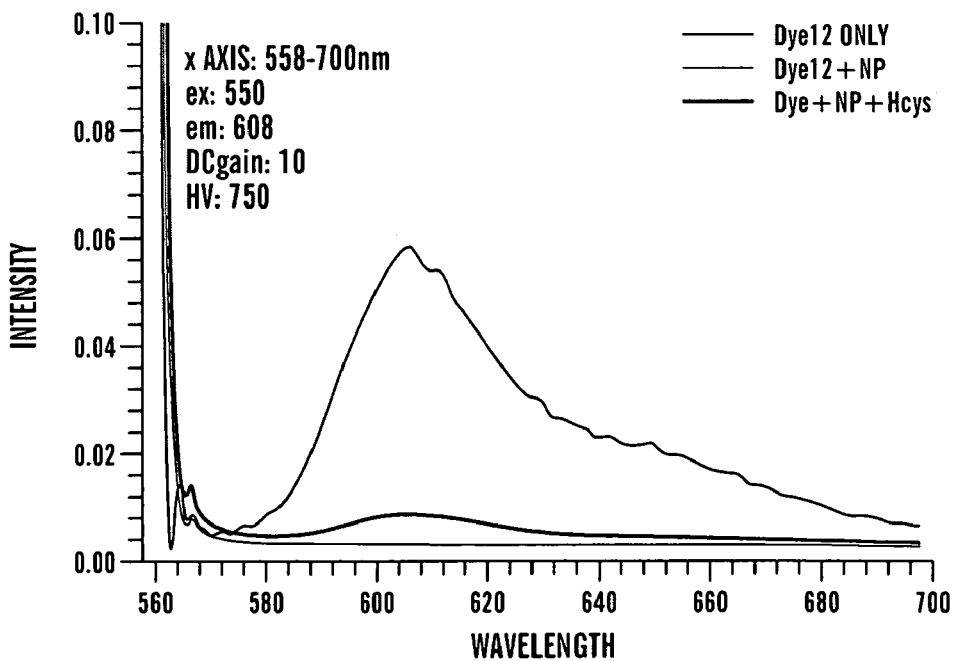
FIG. 8B shows Fluorescence spectra for the solution of ICD-$Au_{nm}$ assembly upon addition of Hcys. [ICD]=0.8 µM, [Hcys]=80 µM.

FIG. 8A represents a set of SERS spectra for the assembly and disassembly of the ICD-$Au_{nm}$ assembly. As reported, the detection of dye molecules itself using SERS without any attachment to silver or gold nanoparticles is unfeasible. However, strong and distinct peaks are observed from the SERS spectrum when the dye molecules are attached to silver or gold nanoparticles. This allows it to act as a reporter molecule in a SERS optical probe. See Kneipp, J., et al., *Anal. Chem.* 77: 2381 (2005), which is incorporated by reference in its entirety. As shown in FIG. 8A, the ICD solution showed no observable peaks. When ICD molecules were added to the $Au_{nm}$ solution, sharp distinct peaks began to be revealed (FIG. 8A). The color changed from a light purple solution to a red/purple solution. The addition of HEys to the system further showed that the ICD molecules was successfully released back into solution due to the absence and removal of all the observable peaks from before (FIG. 8A). The final solution changed from the red/purple (without Hcys) to a blue solution (with Hcys). Similarly fluorescence spectroscopy (FIG. 8B) shows partial recovery of the fluorescence intensity (from red to green in the spectra), demonstrating the viability of the thiol-induced disassembly of ICD-$Au_{nm}$. However, the recovery is rather small suggesting a limited release of ICDs by Hcys. It also suggests that the overall network structure is very stable. The origin for this stability likely reflects the binding strength of the J-aggregates of ICDs surrounding the nanoparticle assembly that makes it hard for Hcys molecules to access the gold surface to exchange with the citrate molecules. It is possible that Hcys replace only those ICD molecules that are near the outer surface of the assembly.

Example 6

Nanoparticle Size Effect

The ICD-$Au_{nm}$ assembly is further analyzed by size dependence using two types of molecularly capped gold nanoparticles (sodium citrate and sodium acrylate) where citrate capped Au nanoparticles having an average size of 13 nm and acrylate capped Au nanoparticles having an average diameter size of 11 nm and 62 nm.

Figure 9A:
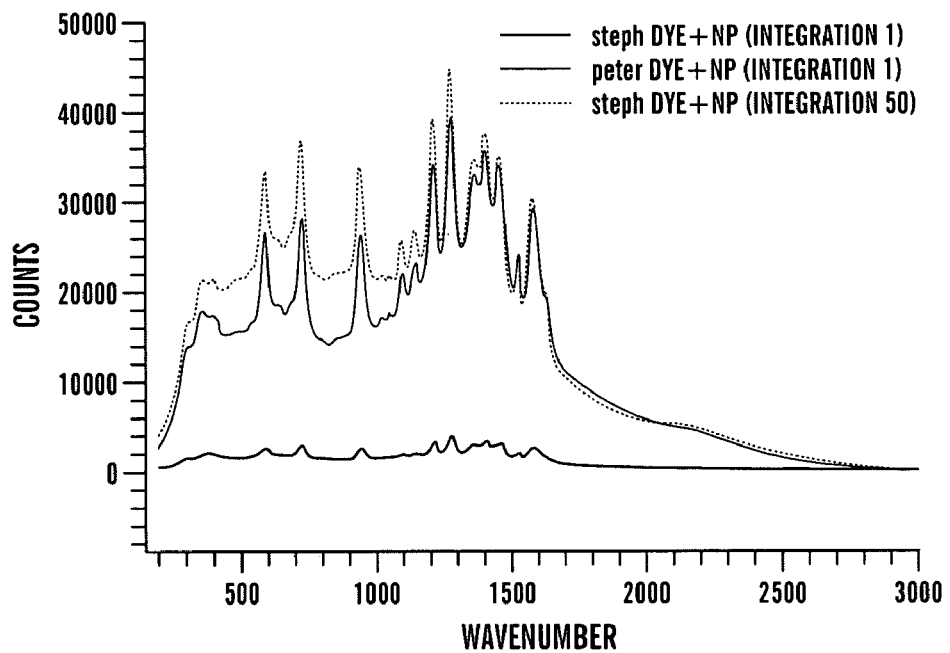
FIGS. 9A-B show a comparison of SERS spectra for ICD-$Au_{nm}$ assembly using $Au_{nm}$ (11 nm) and $Au_{nm}$ (62 nm) [ICD]=0.6 µM (FIG. 9A) and $Au_{nm}$ (11 nm) (FIG. 9B) [ICD]=0.6 µM (FIG. 9B).

FIG. 9A represents a set of SERS spectra for the ICD-$Au_{nm}$ assembly of 13 nm $Au_{nm}$ and 11 nm $Au_{nm}$ capped with citrate and acrylate, respectively. As presented, under the same integration time, the ICD-$Au_{nm}$ assembly using 62 nm $Au_{nm}$ revealed intense peaks at various positions while the peaks for ICD-$Au_{nm}$ assembly using the 13 nm $Au_{nm}$ were diminutive and unresolved. By increasing the integration time from 1 to 50 for the 13 nm $Au_{nm}$, the same peak intensity was achieve as in the 62 nm $Au_{nm}$.

Figure 9B:
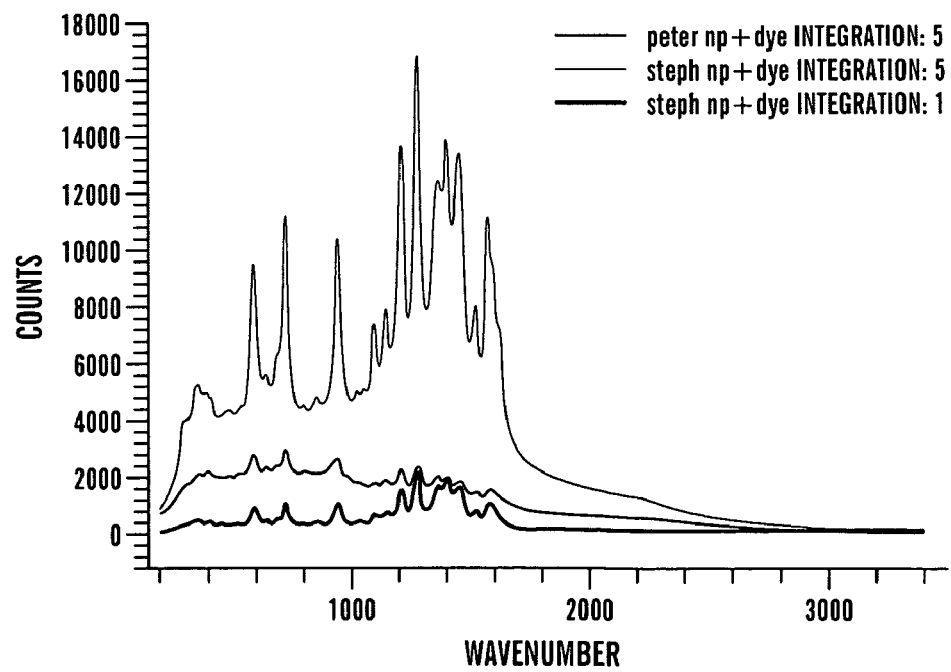

In another experiment, the size effect of the 13 nm and 11 nm size $Au_{nm}$ was studied. This experiment again proves the importance of different sizes in the assembly process. As shown in FIG. 9B, at the same integration time, the ICD-$Au_{nm}$ assembly using 13 nm $Au_{nm}$ revealed intense peaks as compared to when the 11 nm $Au_{nm}$ was utilized. In order to achieve the same intensity as the ones in 11 nm Aunt, the integration time for the 13 nm $Au_{nm}$ had to decrease from an integration time of 5 to 1. While more experiments are needed to study the size dependent effect, this study is in agreement with the study done by Liu and coworkers where different peak intensities are being observed when different sized metal particles are utilized. See Zhu, T., et al., *Mol. Cryst. and Liq. Cryst.* 337: 237 (1999), which is hereby incorporated by reference in its entirety.

Figure 10A:
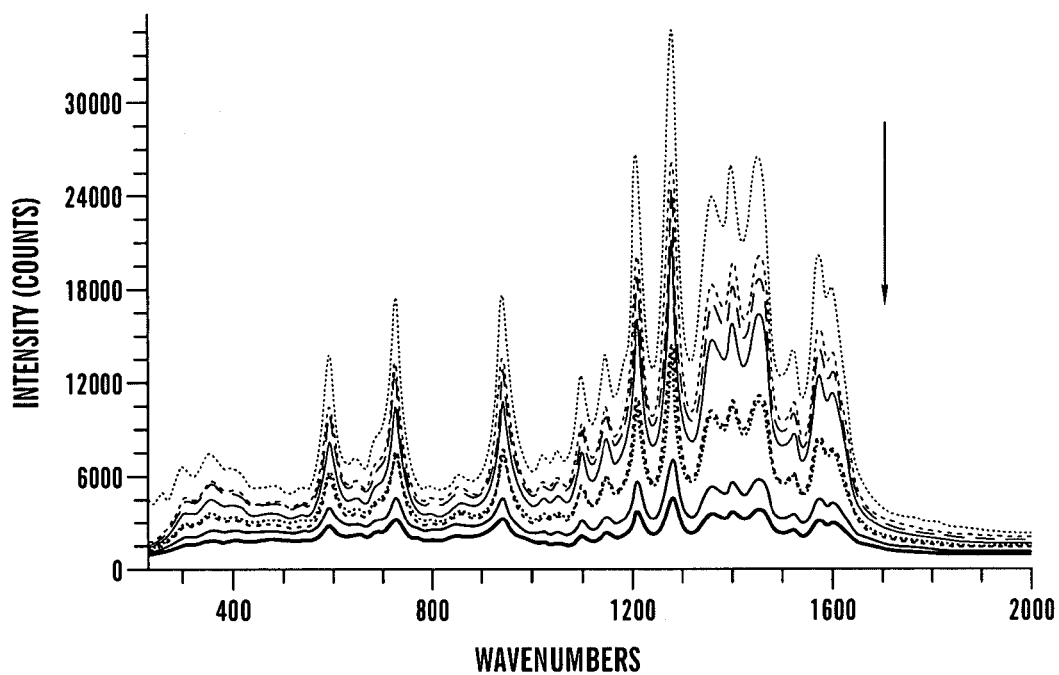
FIG. 10A-B show SERS spectra for an ICD-$Au_{nm}$ assembly.
Figure 10B:
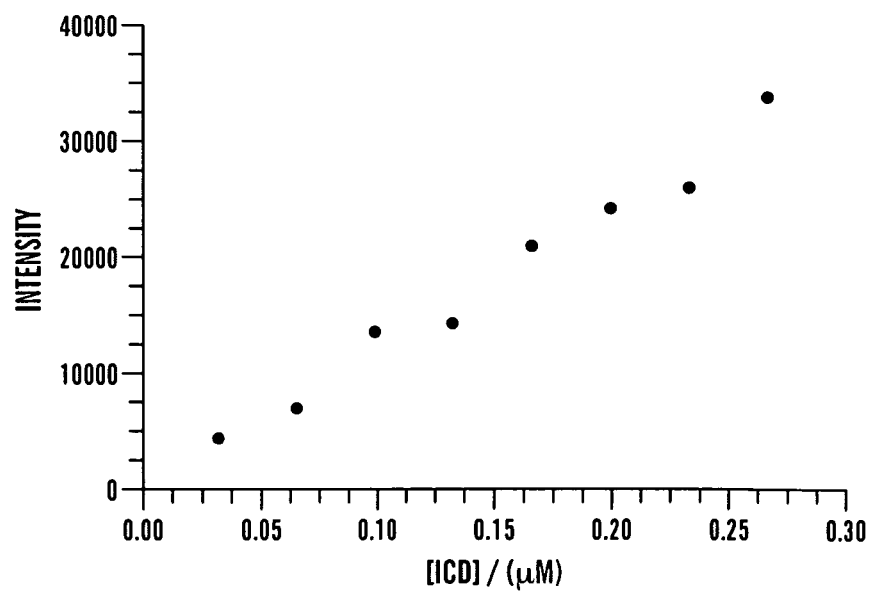

The measurement of the surface enhanced Raman scattering spectra of the dye-nanoparticle assembly reveal further information for assessing both the mechanistic aspect of the assembly and the potential application of the system as SERS nanoprobes. FIG. 10 shows a preliminary set of SERS data for $Au_{nm}$ solution (2.5 nM) upon addition of different concentrations of dyes. It is evident that the intensity of the bands of the dye molecules increases with the dye concentration, which is largely linear at the concentration range. Based on the calculation earlier, a monolayer or sub-monolayer coverage (~175 ICD) is expected for the concentrations of the dyes in comparison with the concentration of the nanoparticles. The experiments also showed that the intensity approaches a plateau as the dye concentration further increases, which serves as an additional piece of evidence for the SERS effect as a result of the adsorption of dyes on the surface of the nanoparticles.

Example 7

Results from Spectrophotometric Titration Experiment

Figure 11:
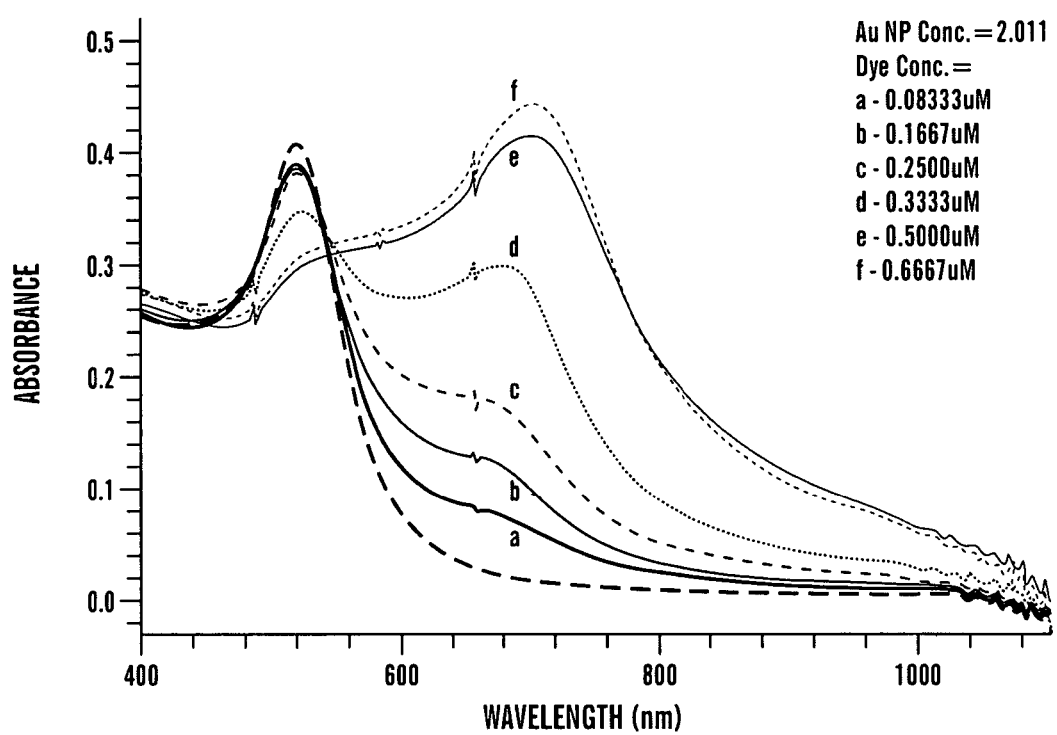
FIG. 11 shows UV-Vis spectra monitoring the last point of the ICD-mediated assembly of $Au_{nm}$ in solutions with different concentrations of dye.

The above color changes can be quantitatively followed by spectrophotometric measurement. FIG. 11 represents a set of spectral evolution for the ICD-gold nanoparticles assembly mediated using different concentration of ICD molecules. The graph shows the last curve of the spectral evolution taken for the mediated assembly at a different dye concentration. The reaction was allowed to continue for thirty minutes.

As the concentration of the dye increases, the reactivity and kinetics of the assembly increases. This is indicated by the decrease of the peak at 520 nm and an increase of the peak at a higher wavelength around 700 nm. The decrease of the 520 nm represents the reduction of the number of free nanoparticles available in the solution as the reaction proceeds. Likewise, the peak around 700 nm increases as the concentration increases, because the particles are assembling and start to form larger size assemblies. As shown, the absorbance at 700 nm is highly dependent on the concentration of dye added. For example, at a low concentration of ICD (0.088 µM), the absorbance at 700 nm is below 0.1 while at high concentration of ICD (0.67 µM), the absorbance at 700 nm is above 0.4.

In each case, the color of the solution changes. This change is a result of the assembly of the nanoparticles as the size, shape, and interparticle distance begin to vary because of different types of interaction. Upon the addition of a low concentration of ICD molecules, little or no color change is observed. The color of the solution also remained red for a week. However, when a high concentration of ICD molecule is added to the nanoparticle solution, the color changes immediately from red to purple or bluish color.

Figure 12A:
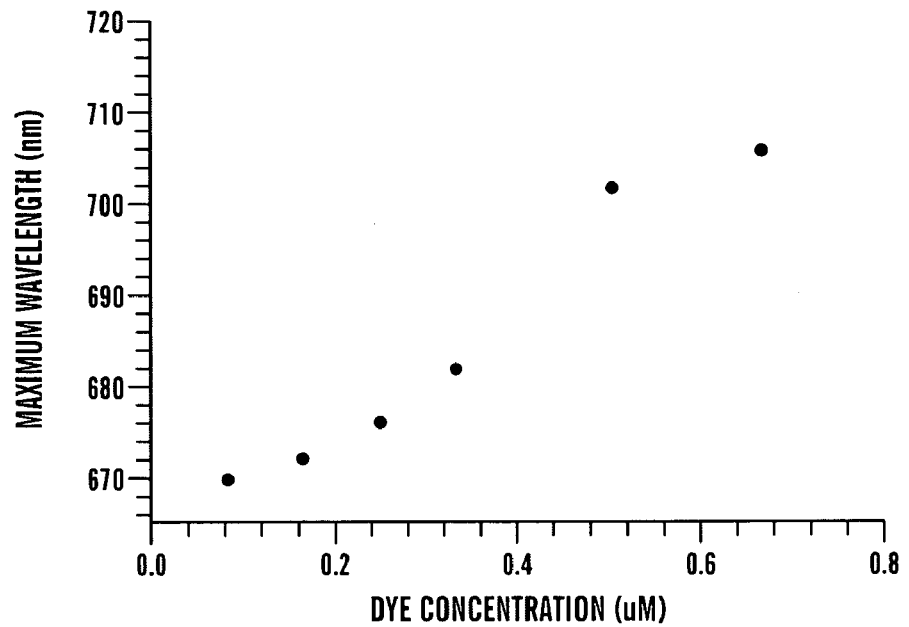
FIG. 12A shows a graph plotting maximum wavelength vs. ICD concentration.
Figure 12B:
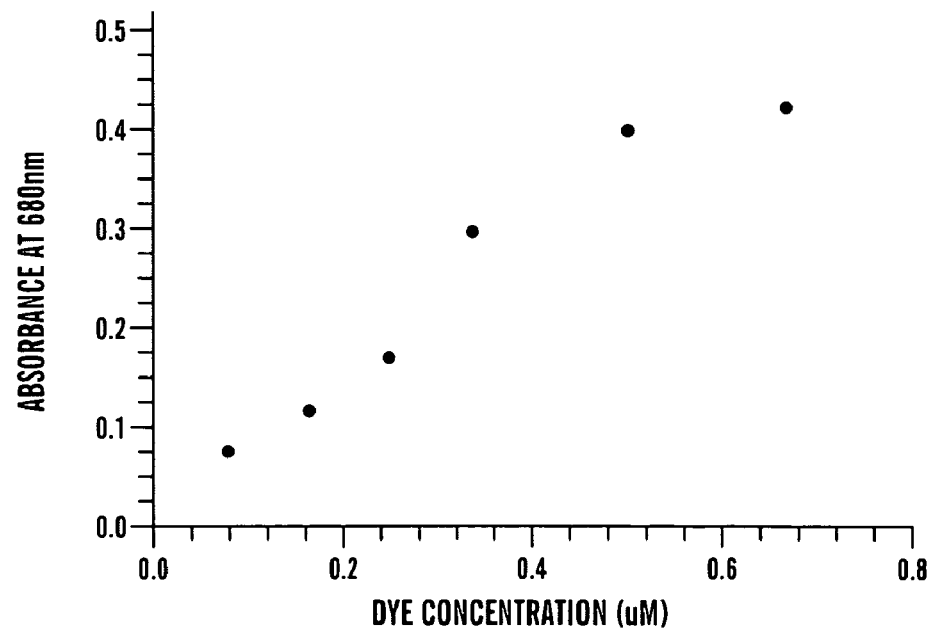
FIG. 12B shows a graph plotting absorbance at 680 nm vs. ICD concentration.

FIG. 12 represents a plot of maximum wavelength vs. the ICD concentration (FIG. 12A) and absorbance at 608 nm vs. the ICD) concentration (FIG. 12B).

FIG. 12A is plotted by taking the maximum wavelength of the last spectral evolution curve of each sample vs. the ICD dye concentration added. As shown, as the concentration of dye increases, the maximum wavelength detected also shifts to a longer wavelength. FIG. 12B, shows a similar feature. However, in this case absorbance vs. the ICD dye concentration was plotted. The absorbance for each curve was taken at 608 nm. As shown in FIG. 12B, as the dye concentration increases, the absorbance at 608 nm increases. This is an indication of an increase in the assembly process.

In this study, the mechanism and interactions of the assembly system are the focus. Reports have shown that ICD molecules are fairly pH insensitive. Therefore, the ICCD molecules will also contribute an overall positive charge on the molecule regardless of its pH condition. However, citrate capped gold nanoparticles are highly sensitive toward pH changes. As previously reported, the citrate has three pKa: $pK_a = 3.1(a_1)$, $4.8(a_2)$, and $6.4(a_3)$. See Lim, I-I. S., et al., *Chem. Mater.*, 17: 6528 (2005), which is hereby incorporated by reference in its entirety. Hence, in this study the effect of pH on the assembly is measured.

Figure 13A:
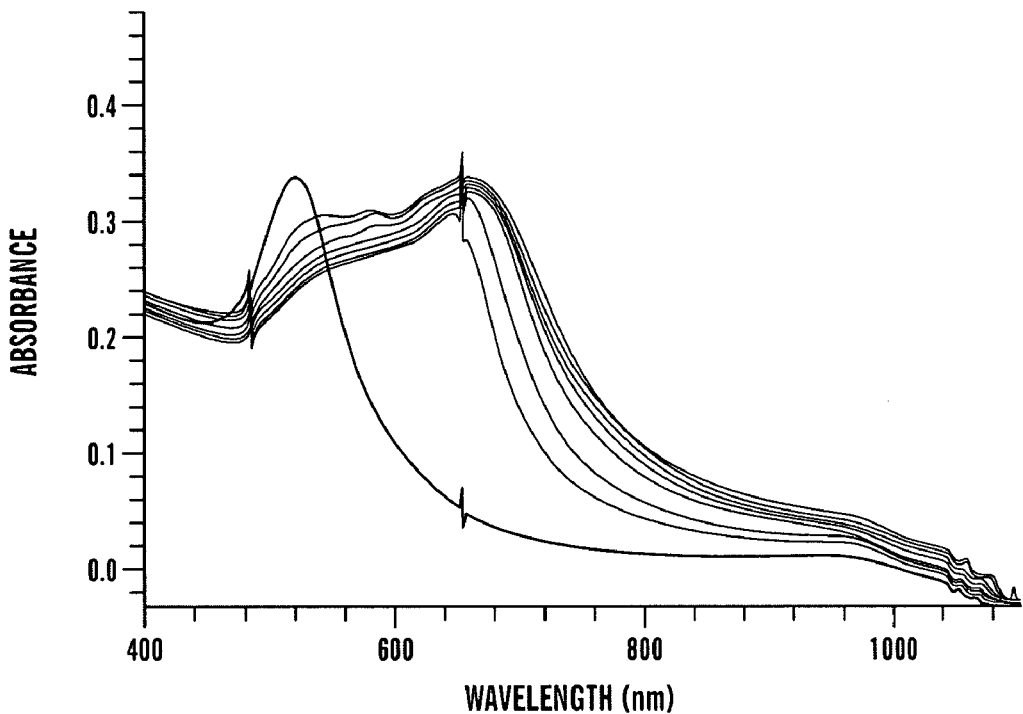
FIGS. 13A-D show UV-Vis spectral evolution of pH dependence for ICD-$Au_{nm}$, assembly.
Figure 13B:
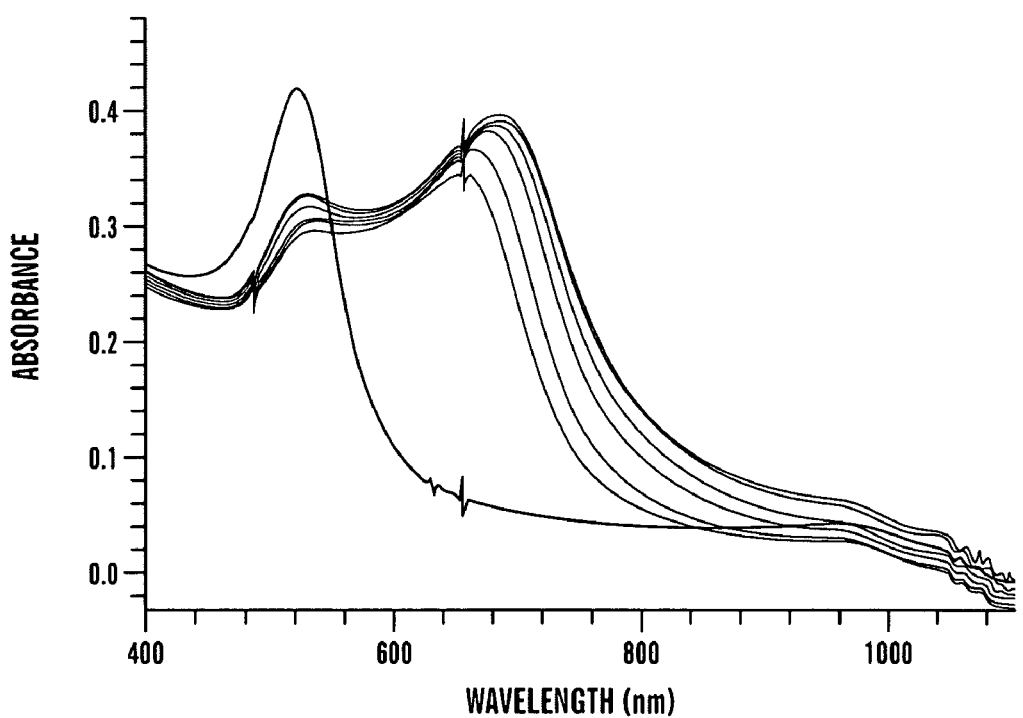
Figure 13C:
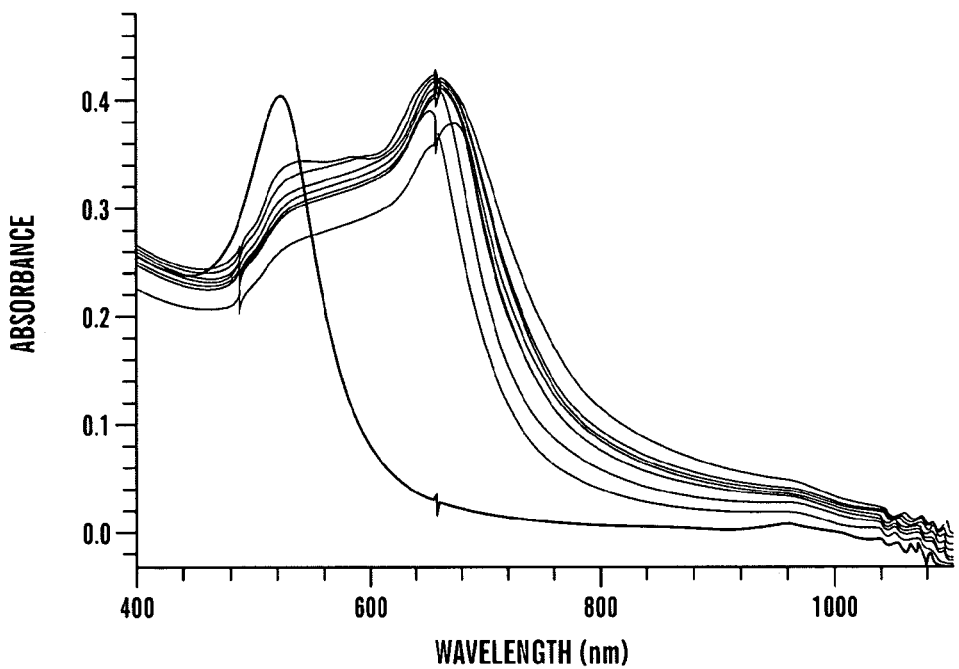
Figure 13D:
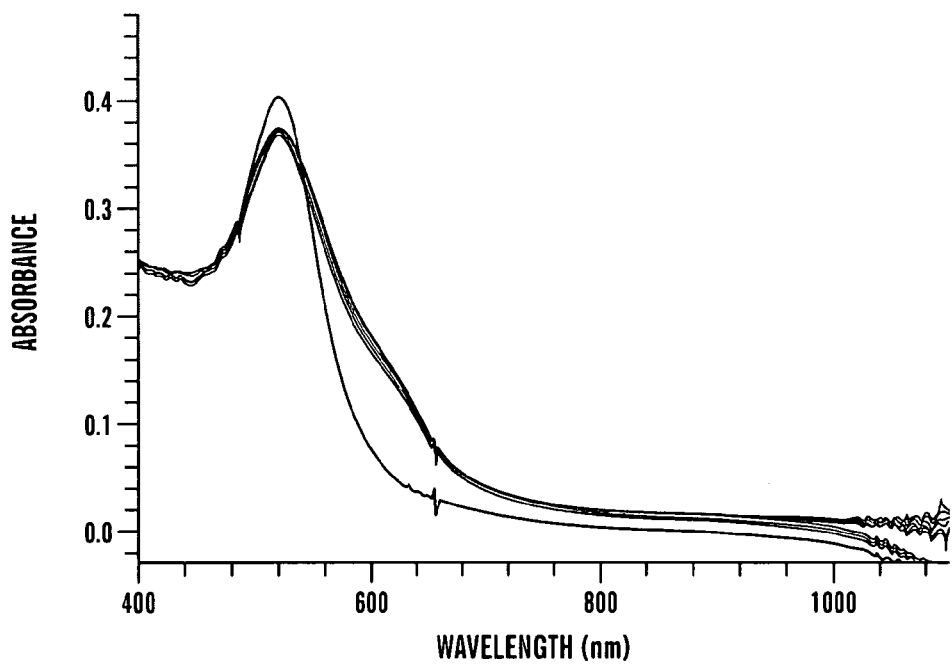

In this experiment, first the pH of the solutions of ICD and gold nanoparticles are changed separately to the designated pH by the addition of HCl or NaOH. After that, the ICD and gold nanoparticles are added quantitatively and using UV-Visible spectroscopy, the spectral evolution change is monitored. A series of pH dependent effects, ranging from pH 3-10, were studied. FIG. 13 represents a set of spectral evolution data when the assembly pH was changed to 9 (FIG. 13A), 4 (FIG. 13B), 5 (FIG. 13C), and 10 (FIG. 13D).

At a pH of 3, all the $CO_2H$ groups on the citrate molecules are protonated. However, due to the instability of gold nanoparticles at low pH, a decrease in reactivity was observed. At a pH of 4 (FIG. 13B), two of the $CO_2H$ group would be protonated. At this pH, a maximum reactivity of the assembly was observed. At the pH of 5, only one $CO_2H$ is protonated. The reactivity observed decreased when the ICD and gold nanoparticles are added together. At the pH of 10, all of the $CO_2H$ groups have been deprotonated. At this pH condition, spectral evolution was not observed. The solutions for pH 3-5 changed color from red to blue/purplish, while the solution for pH 10 remained red for weeks.

Figure 14:
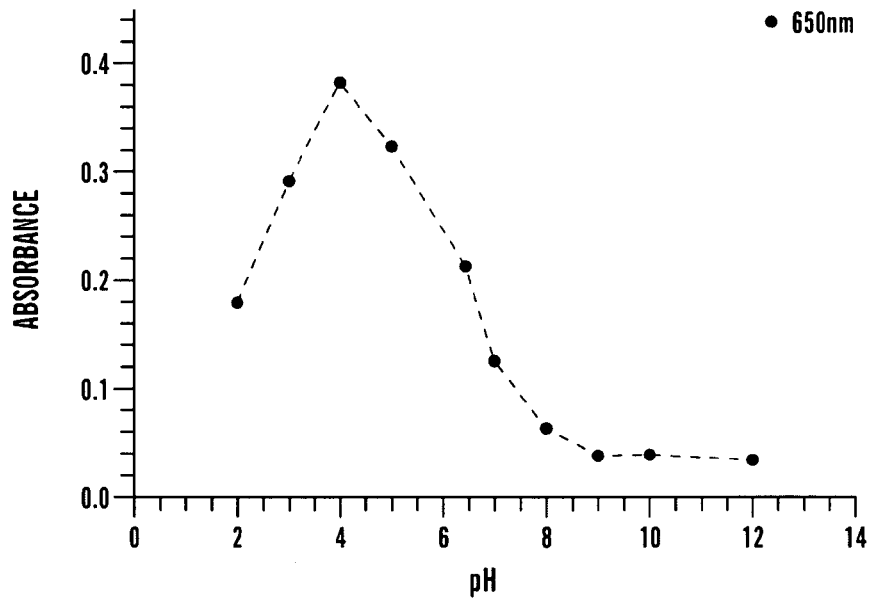
FIG. 14 shows a graph plotting absorbance at 650 nm vs. pH for ICD-gold nanoparticles assembly.

FIG. 14 shows a plot of the absorbance taken at 650 nm vs. the pH of the ICD-gold nanoparticles assembly. The maximum in absorbance is obtained when the pH condition of the assembly is at 4. This piece of evidence reveals that the protonation and deprotonation of the COAH group on the citrate molecules play an important role in the assembly process of the ICD-gold nanoparticle assembly.

There are two main conclusions that can be obtained from this work. First, using the UV-spectrometer, the reaction between the gold nanoparticles and the dye with varying concentrations was followed. That the interaction between the gold nanoparticles and the indolenine cyanine dye is dependent on both the concentration as well as the pH of the solutions was shown. By changing the concentration of the dyes, the reaction can be manipulated to react either rapidly or slowly. As the concentration increases, the reaction is more rapid, and there is a more noticeable color change from red to blue. Secondly, the pH determines the effectiveness of the interaction between the molecules, and varies from pH 2 to pH 12. As the pH increases from 2 to 5, the reaction becomes more effective and a color change is visible. As the pH increases from 6 to 12, the effectiveness of the reaction decreases, and eventually, the reaction ceases to occur.

Once the conditions affecting the dye and nanoparticle interaction can be determined and analyzed, the effect of these conditions on aggregation must also be understood before this dye is ready for application. With this knowledge, it is possible to perform further research on the interaction between the dye and gold nanoparticles. The study will be useful for potential applications in the biomedical field. The dye can serve as not only an indicator but also a type of target for the nanoparticles once inside of the human body.

Example 8

Fluorescence Data

Even though the final volume is not constant due to the incremental addition of $Au_{nm}$ into the solution, the intensity was corrected with respect to the ICD dye concentration of 1.0 µM. See Table 2.

TABLE 2

| Dye [µM] | Intensity at 606 nm | Corrected Intensity at 606 nm |
|---|---|---|
| 1 | 0.4381 | 0.4381 |
| 0.97 | 0.3337 | 0.344 |
| 0.95 | 0.2457 | 0.258 |
| 0.93 | 0.1781 | 0.192 |
| 0.92 | 0.1503 | 0.164 |
| 0.91 | 0.1233 | 0.136 |
| 0.90 | 0.1039 | 0.115 |
| 0.89 | 0.0885 | 0.099 |
| 0.88 | 0.0708 | 0.080 |

Figure 15:
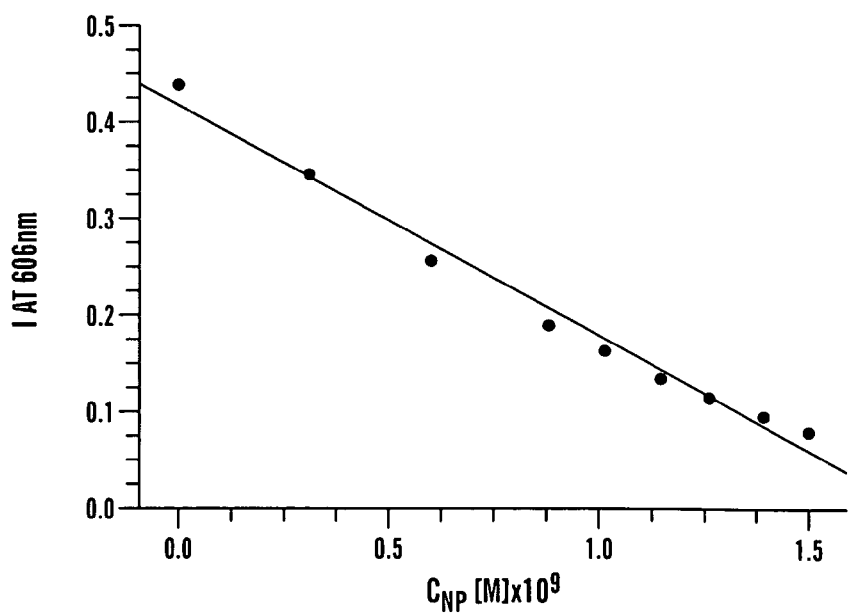
FIG. 15 shows a graph plotting the measured fluorescence intensity at 606 nm vs. concentration of $Au_{nm}$ (linear regression: y=−2.35×$10^8$x+0.416). The corrected [ICD]=1.0 µM.

FIG. 15 shows a plot of the corrected intensity vs. the $Au_{nm}$ concentration added. It displays a linear relationship and fitted well with the experimental data, with slope=-k'b $N_0 \Gamma_0 SA_{NP}$ and y-intercept=k k'b($C_0$-1/K). Using the slope and the y-intercept values obtained and the other parameters, $C_0 = 1 \times 10^{-6}$ M; $\Gamma_0 = 4.43 \times 10^{-11}$ moles/cm$^2$ and $SA_{NP} = 3.5 \times 10^{-12}$ cm$^2$, k'b was found to be $2.52 \times 10^6$ M$^{-1}$, and K to be $1.2 \times 10^6$ M$^{-1}$. The quantum yield ($\Phi$) of the dye is further calculated using $P_0 = 38.68$ and $\epsilon_{ICD} = 1.15 \times 10^5$ M$^{-1}$ cm$^{-1}$, which was found to be 0.25.

Figure 16:
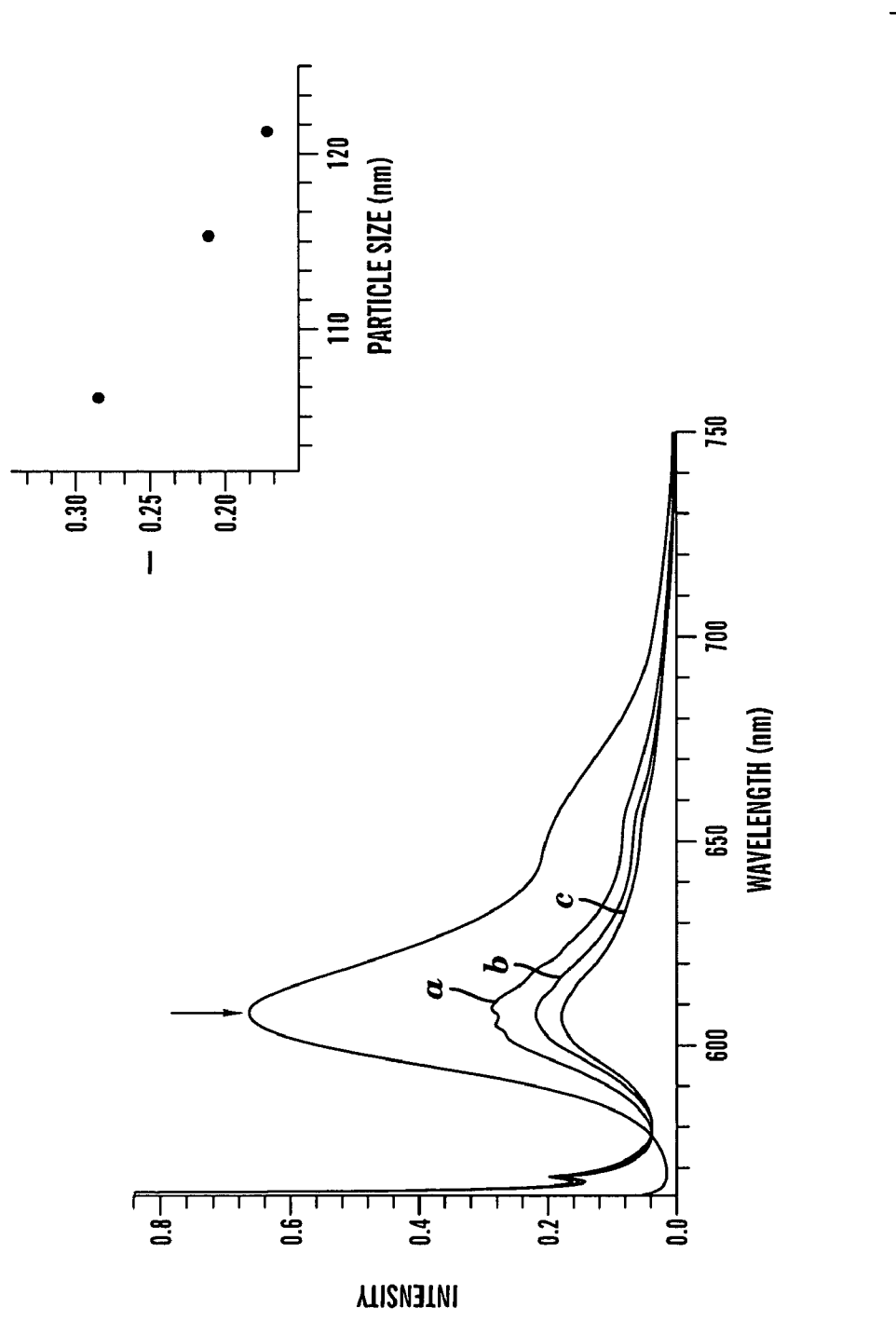
FIG. 16 shows spectra of fluorescence quenching for $Au_{nm}$ of 10.6 nm (a), 11.5 nm (b), and 12.1 nm (c) sizes. [ICD]=1.0 µM. Insert: Intensity (1) at 608 nm vs. $Au_{nm}$ size (nm). The arrow indicates the direction of the spectral evolution with time.

It is known that the quenching is also highly dependent upon the size of the metal nanoparticles. A series of experiments were performed where the concentrations of $Au_{nm}$ and ICD is kept constant while the particle sizes were varied. FIG. 16 shows a set of data. The data seem to suggest that as the core size of $Au_{nm}$ increases, the fluorescence intensity decreases. The calculated quenching efficiency under the experimental condition was found to be 56%, 67%, and 73% for $Au_{nm}$ core sizes of 10.6 nm, 11.5 nm, and 12.1 nm, respectively.

Example 9

Optical Absorption Properties

Figure 17:
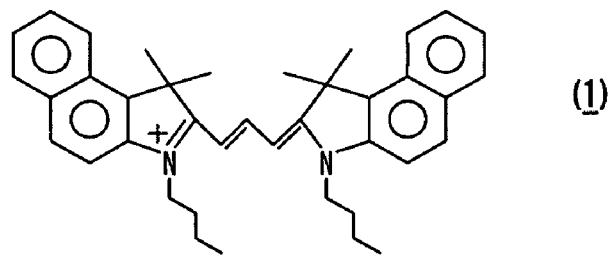
FIG. 17 shows the structural formulae for the four different cyanine dyes studied in this work, with structure (1) in FIG. 17 showing ICD.
Figure 17:
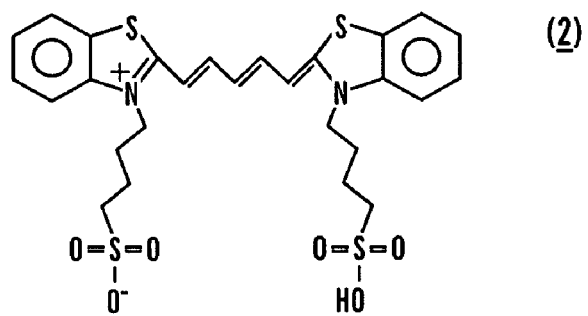
Figure 17:
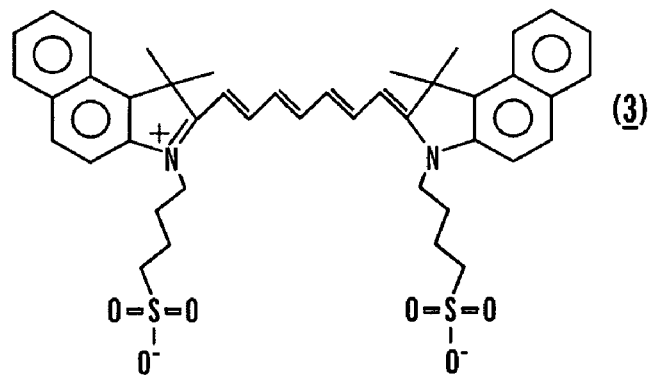
Figure 17:
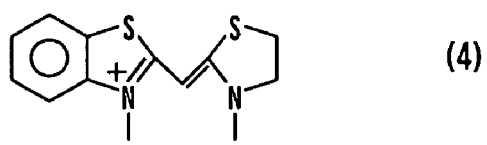

The reactivities of the citrate-capped gold nanoparticles with four different structures of cyanine dyes were examined. As shown in FIG. 17, the structures for the four dye molecules (1 (i.e., ICD), 2, 3, and 4) examined differ in terms of the nature of the charge and the size of the conjugated moiety. These differences are shown below to exhibit profound differences in terms of the optical absorption data which characterize the reactivities of the dyes with the nanoparticles.

Figure 18:
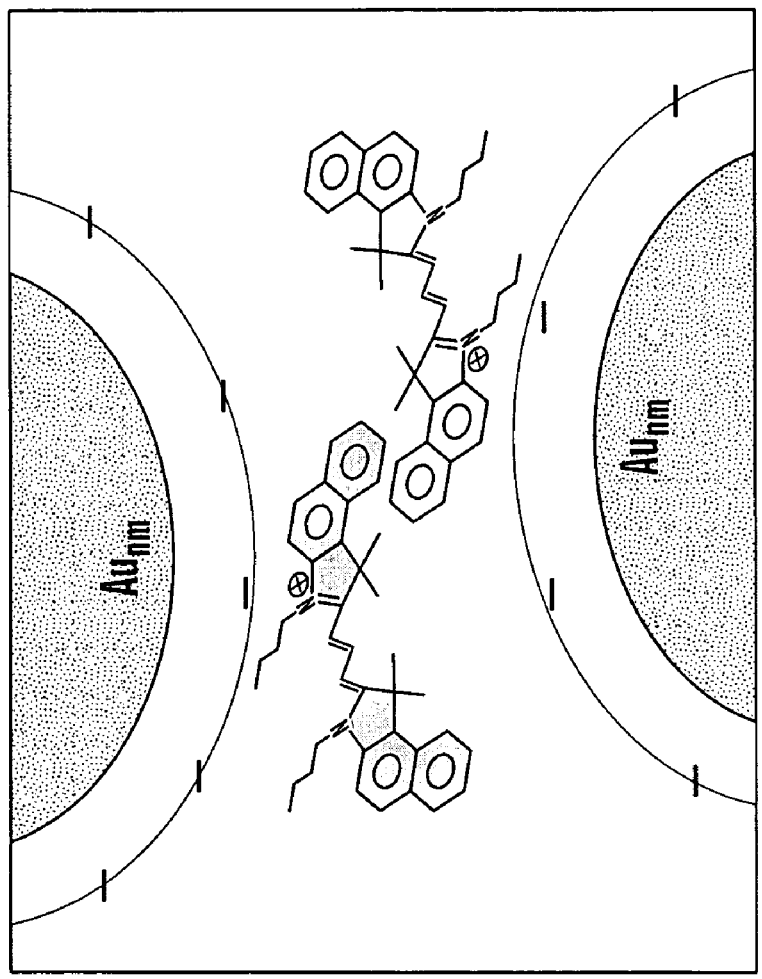
FIG. 18 shows a schematic illustration of the electrostatic and π-π interactions for the adsorbed ICDs on gold nanoparticles capped with negatively-charged groups (not to scale).
Figure 19A:
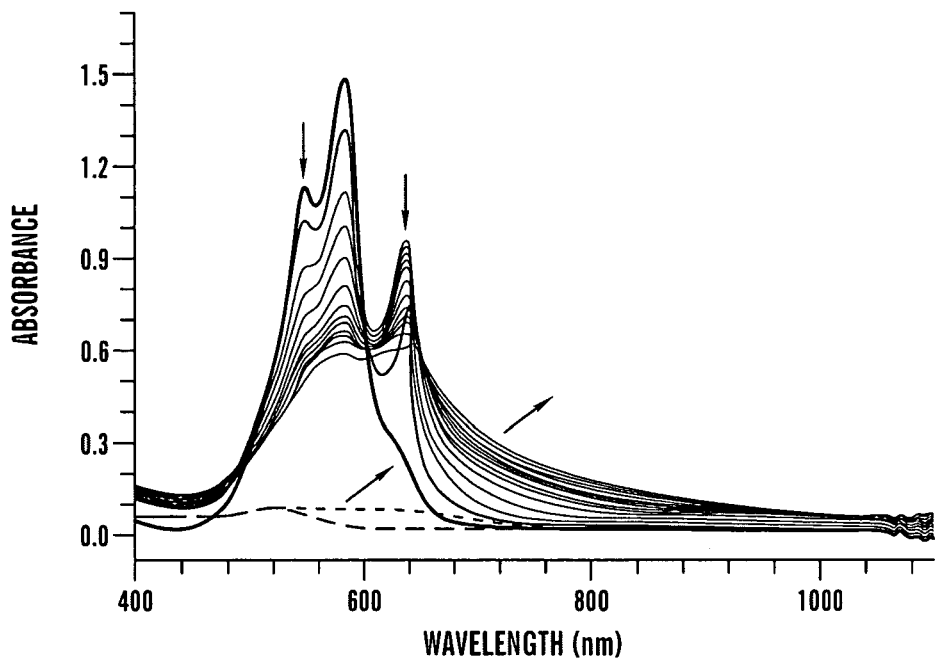
FIGS. 19A-B show UV-Vis spectra monitoring the ICD-mediated assembly of $Au_{nm}$ in solutions.
Figure 19B:
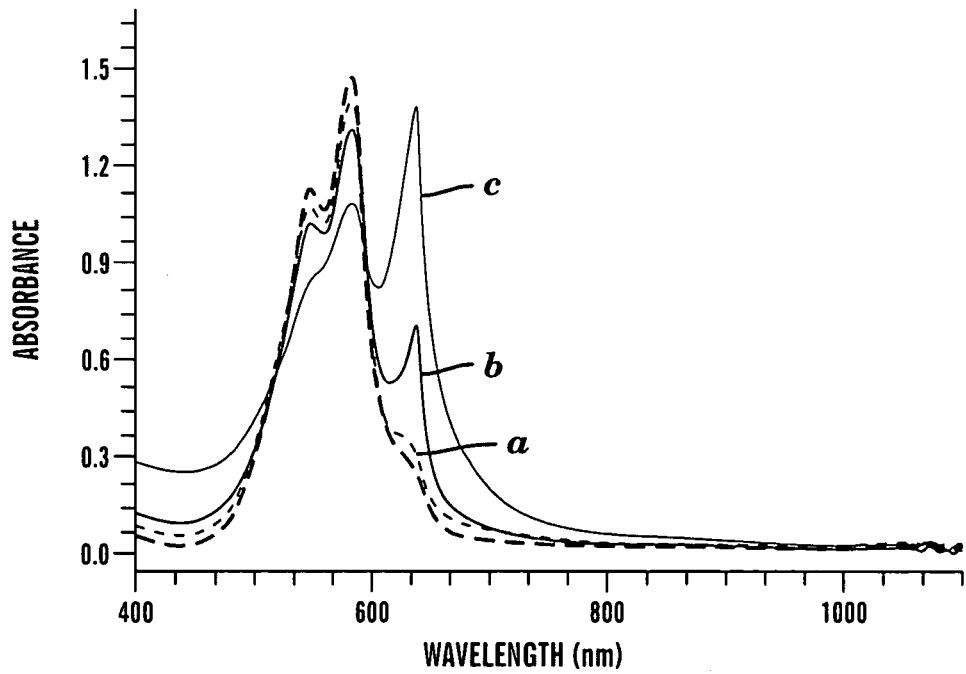

As shown in FIG. 19A for a typical set of UV-Vis spectra, the spectrum of ICD (1) exhibits two absorption bands at r 545 and 582 nm due to $\pi$-$\pi^*$ transitions. A weak shoulder band can also be identified at $\lambda = \sim 630$ nm. Upon addition of $Au_{nm}$ into the ICD-solution, the spectra reveal a dramatic spectral evolution depending on the concentration of the dye. At a high concentration of ICD (e.g., 9.8 µM), a red-shifted band is evident at 635 nm. The absorbance of this band increases in the first 30 seconds to a maximum and is followed by subsequent decrease. The absorbance decrease of this band is accompanied by spectral changes in two regions. There is a gradual increase of absorbance or broadening of the band in the longer wavelength region (640-800 nm). This evolution is clearly at the expense of the absorbance decrease in the 500-600 nm region. To assess whether there is a contribution of the surface plasmon (SP) resonance band of $Au_{nm}$ to the observed spectral evolution in the long wavelength region, the spectra for a solution of $Au_{nm}$ with an identical concentration (0.42 nM) upon addition of a lower concentration of ICD (0.64 µM) were compared with the spectral evolution. As shown by the dashed curves in FIG. 19A, much smaller absorbance values were obtained. This indicates that the above spectral evolution is basically a result of the dyes due to interaction of the nanoparticles. As a result, the contribution of the surface plasmon resonance band of the nanoparticles can be ruled out. It is also found that the intensity of the band at ~630 nm is highly dependent on the concentration of $Au_{nm}$ added into the solution. As shown in FIG. 19B, the absorbance for the band at ~630 nm recorded within the 10 seconds increases with the concentration of $Au_{nm}$. On the basis of the above observations and the red-shift characteristic, the band at ~630 nm is clearly associated with the formation of J-aggregates from the adsorbed dyes. See Kobayashi. T., Ed., *J-Aggregates*, World Scientific Publishing Co.: Singapore (1996), which is hereby incorporated by reference in its entirety. The observation of the J-band thus demonstrates the formation of J-aggregates of the dyes as a result of the reactivities of dyes with nanoparticles (see FIG. 18).

It is important to note that the observation of the peak-shaped J-aggregate band is in fact consistent with the previous experimental observation for silver nanoparticles with other cyanine dyes and the theoretical modeling of the coupling between surface plasmon of the metal core and molecular exciton of the dye. See Kometani, N., et al., *Langmuir* 17: 578 (2001) and Wiederrecht, G. P., et al., *Nano Lett.* 4; 2121 (2004), which are hereby incorporated by reference in their entirety. A peak-shaped J-band develops when the J-band exciton absorption is located at a slightly longer wavelength than the surface plasmon resonance absorption, which is indeed the case for this dye-nanoparticle system. Also note that the red-shifted J-band for the dye-nanoparticle system, as shown in FIG. 19, is initially very sharp. This is in agreement with that of the red-shifted J-band that appears as an intense narrow absorption band due to the motional narrowing. See An, B.-K., et al., *J. Am. Chem. Soc.* 124: 14410 (2002), which is hereby incorporated by reference in its entirety. However, the fact that this band became relatively broad and weak in the prolonged assembly process suggests that the dye molecules could be oriented in a less optimal way of J-aggregation. Lattice disorder is often considered as one of the possible reasons for this type of reorganization. See Knapp, E. W. *Chem. Phys.* 85: 73 (1984), which is hereby incorporated by reference in its entirety. Similar spectral characteristics were reported for J-aggregates of nanoparticles derived from 1-Cyano-trans-1,2-bis-(4-methylbiphenyl)-ethylene. See An, B.-K., et al., *J. Am. Chem. Soc.* 124: 14410 (2002), which is hereby incorporated by reference in its entirety. Therefore, the initially sharp band is in agreement with the motional narrowing, whereas the subsequent broadening is due to lattice disorder as a result of the surface reorganization of the adsorbed dyes. While it is possible that there are contributions to the J-band from intermolecular (dyes on the same particle) and intramolecular (dyes between two particles) J-aggregations the observed strong dependence of the J-band intensity on the concentration of nanoparticles substantiates the formation of interparticle J-aggregations.

Figure 20A:
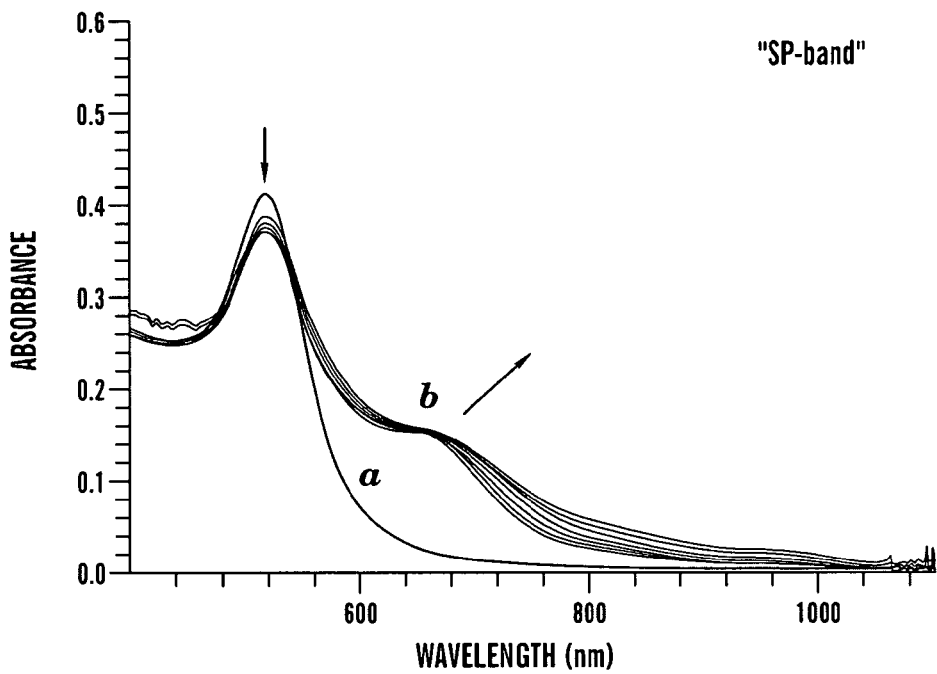
FIGS. 20A-D show UV-Vis spectra monitoring the SP-band of the ICD-mediated assembly of $Au_{nm}$ in solutions.
Figure 20B:
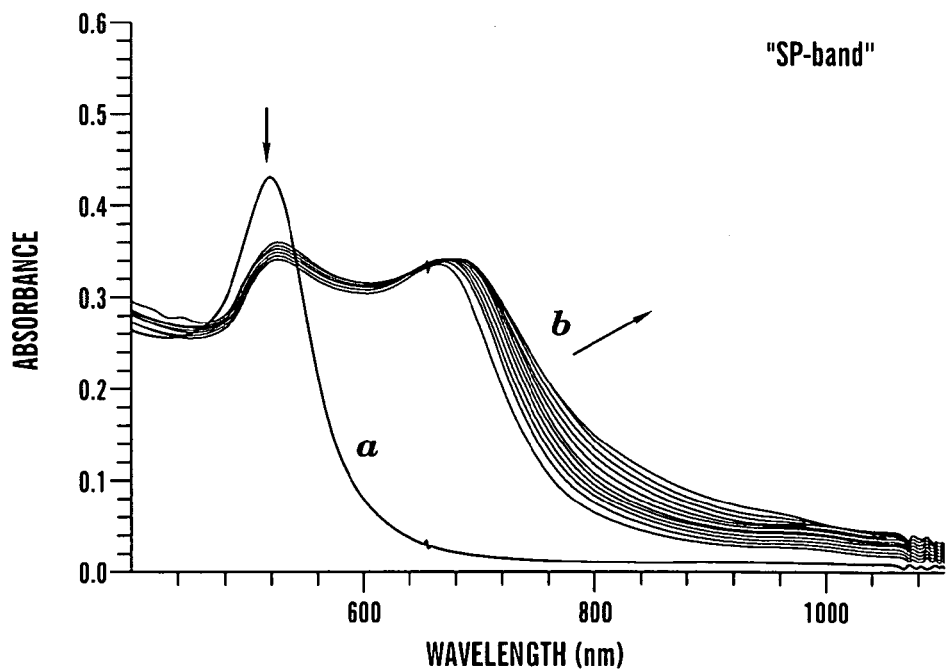
Figure 20C:
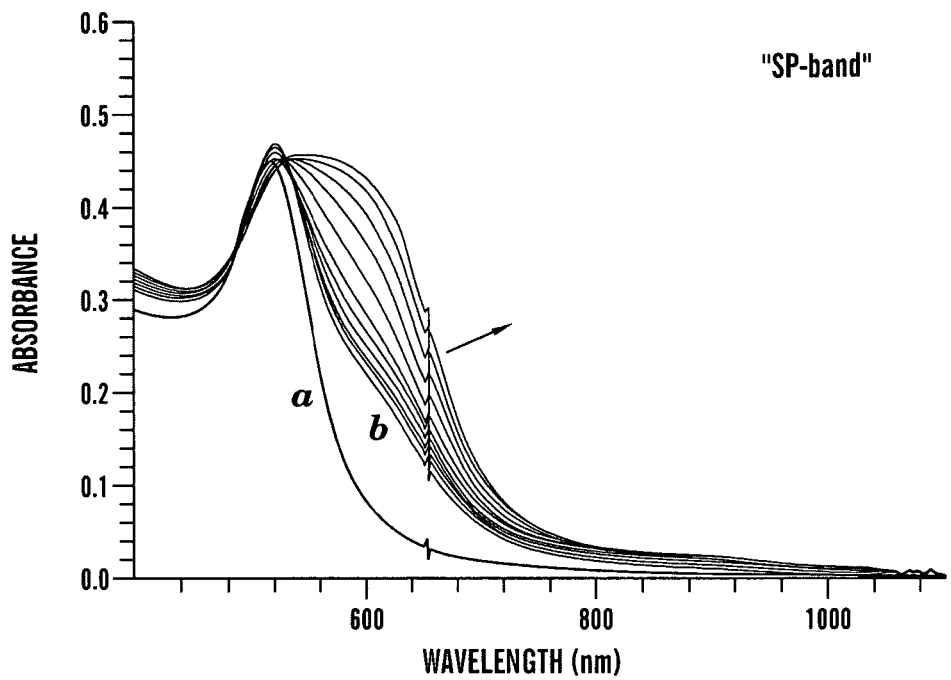
Figure 20D:
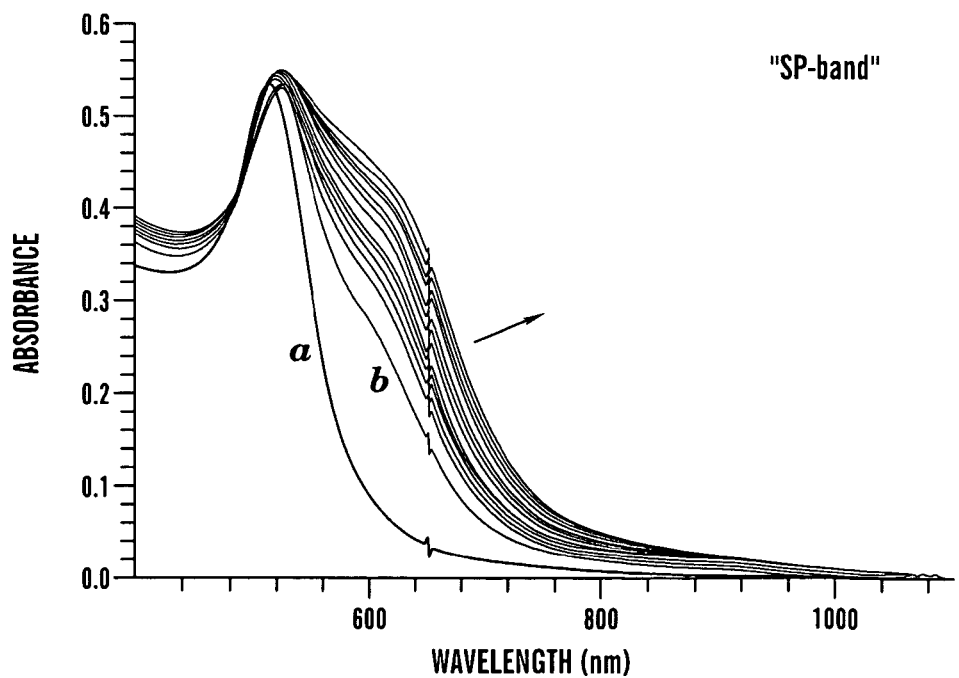

It is important to emphasize that for the two dye concentrations in the above data, i.e., high (e.g., 9.8 µM) and low (e.g., 0.64 µM) concentrations, the high concentration case shows two bands from the dye molecules, whereas the low concentration case shows one band from the Au nanoparticles. The bands from the dye are too weak to be seen in the latter case. Gold nanoparticles exhibit a strong surface plasmon resonance band at 520 nm, the wavelength and absorbance of which strongly depend on the size, shape, interparticle distance, and the surrounding dielectric medium constant. See Maye, M. M., et al., *J. Phys. Chem. B* 109: 2578 (2005) and Zhang, F. X., et al., *Analyst* 127: 462 (2002), which are hereby incorporated by reference in their entirety. FIG. 20 shows a representative set of spectral evolution for ICD-mediated assembly of $Au_{nm}$ in solutions of different concentrations of ICDs and $Au_{nm}$. It is important to point out that while the spectral evolution for both J-band of the dyes and SP-band of the nanoparticles appears at the higher wavelength region, they are distinctively different in band shape and intensity. There are three general characteristics for the SP-band evolution. First, upon addition of ICDs into the solution, new bands emerge at wavelength longer than the SP band of $Au_{nm}$. A band emerges at 680 nm accompanying the decrease of the 520 nm band. Both the band at 520 nm and the band at ~630 nm are from the SP band of Au nanoparticles, not from the dye molecules. A clear isosbestic point is observed at 660 nm, indicating the reactivity involving two species (reactant and product). Second, the wavelength for the new bands is strongly dependent on the concentration of dye. The higher the dye concentration is, the longer the wavelength of the new bands appears. Thirdly, at a relatively high concentration of dye, the increase and broadening of the new bands are accompanied by a decrease of the SP band of $Au_{nm}$. The dependence of the spectral properties on the concentration of $Au_{nm}$ was also examined (FIGS. 20C and D). The general characteristic of the spectral evolution showed some similarities, including increase in absorbance for the new band at ~620 nm, which is accompanied by a distinct color change from red to purple. A close examination reveals, however, subtle differences. For example, the absorbance for the SP band of $Au_{nm}$ at 520 nm remained largely unchanged. The spectral evolution was also accompanied by a distinct color change, indicative of the formation of larger-sized assemblies of nanoparticles. The solution changed from red to purple at lower concentration, which remained soluble after 5 hours, and from red to blue at higher concentration, which precipitated within 30 minutes.

The comparison of the spectral evolution data for several different dyes provided important insights for assessing the structural effects. First, the use of a cyanine dye with a similar structure but different charges, e.g., neutral (i.e., 2) and negatively charged (i.e., 3) dyes, did not lead to any observable reactivity. The absence of any spectral evolution is due to the lack of electrostatic interaction between the dye molecule and the nanoparticles, demonstrating the important role played by the electrostatic interaction in the reactivity. The addition of NaCl (10 mM) to the solution of $Au_{nm}$ and dye (3) also failed to cause any observable aggregation of the nanoparticles. Second, the use of a cyanine dye with a similar structure but smaller $\pi$-systems on both ends of the molecule (e.g., 4) did not show observable spectral evolution under the same experimental condition as in the case of the measurement for dye 1. It showed observable spectral evolution only when a much higher concentration of the dye (>3×) was used. This finding suggests that in addition to electrostatic interaction, other molecular interactions (e.g., $\pi$-$\pi$ interaction) involving the dye molecules have also played an important role in the spectral evolution.

To further demonstrate that the electrostatic interaction is not the only factor contributing to the spectral evolution and the driving force for the assembly process, experiments using other different positively-charged molecules were performed. Examples of such molecules included tetramethylammonium bromide and tetrabutylammonium tetrafluoroborate, both of which have a strong ion-pairing effect with negatively charged groups but also relatively hydrophobic. The results of these experiments did not show any spectral evolution, even at much higher concentrations, demonstrating that the spectral evolution for the ICD-$Au_{nm}$ assembly is not simply due to surface neutralization effect. Since the presence of electrolytes often exerts a specific intermediate bridging role in addition to any non-specific double compression, this issue is further assessed by studying the spectral evolution as a function of salt concentration (e.g., 0.001 to 0.01 M NaCl). No spectral evolution was detected in this concentration range in the absence of ICD dyes. Note that this salt concentration range is much higher than the dye concentration (<1 µM). The ratio of [ICD] to [$Au_{nm}$] used in the experiment was ~83, which translates to ~0.1 positively-charged nitrogen anchored on ICD per citrate group capped on $Au_{nm}$ (ICD has 1 positive charge while the ~11.5-nm $Au_{nm}$ can theoretically accommodate 1250 citrate molecules). This suggests that the amount of positive charges is one-order of magnitude lower than the negative charges on the nanocrystals surface. The experimental data showed that as the salt concentration increased, the spectral evolution displayed a trend of subtle shift of the ~700-nm band toward longer wavelength, indicating the formation of increased assembly. It is well known that the effective diffuse-double layer thickness is inversely proportional to the square root of the electrolyte concentration. A higher salt concentration compresses the Debye radius (screening distance) and reduces interparticle separation distance. At a low salt concentration, the double layer is less compact; at a high salt concentration, the double layer is more compact. The fact that the dye molecules can disrupt the compact diffuse double layer of ions and solvating molecules and lead to more extensive assembly demonstrates that the electrostatic interaction between the positively-charged dyes and the negatively-charged nanoparticles is indeed facilitated by the presence of salt. This leads to the subsequent interparticle interactions via a combination of the $\pi$-$\pi$ interaction and the hydrophobic interaction of the dyes on the nanocrystal surfaces.

On the basis of the optical absorption data, a sequential two-step assembly process is believed to be responsible for the overall spectral evolution, (1) adsorption of ICD on gold nanoparticles largely driven by electrostatic interaction; and (2) interparticle linkage of the ICD-capped nanoparticles largely driven by a combination of J-aggregation and hydrophobic interactions. The latter step must be a slow process as evidenced by the gradual spectral evolution and its concentration dependence. The reason for the slow assembly is associated with the formation of J-aggregates of the adsorbed ICDs via $\pi$-$\pi$ interactions was confirmed by the J-band as shown in FIG. 19. See Kobayashi, T., Ed., *J-Aggregates*, World Scientific Publishing Co.: Singapore (1996), which is hereby incorporated by reference in its entirety. For the first step, it is a direct adsorption of the positively-charged ICD on the negatively-charged $Au_{nm}$, which does not involve exchange of ligands with the capping molecules.

Example 10

Morphological and Structural Properties

Figure 21C:
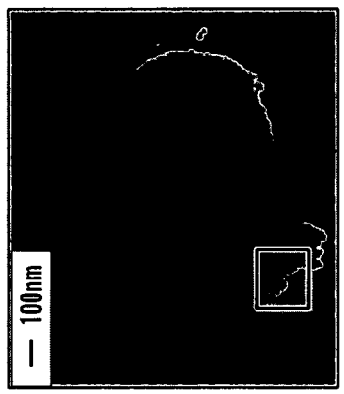
FIGS. 21A-F show TEM images for samples from ICD-mediated assembly of $Au_{nm}$ in solutions with different [ICD]=0 (FIGS. 21A-B), 0.16 (FIGS. 21C-D), and 0.31 μM (FIGS. 21E-F). [$Au_{nm}$]=3.1 nM.
Figure 21F:
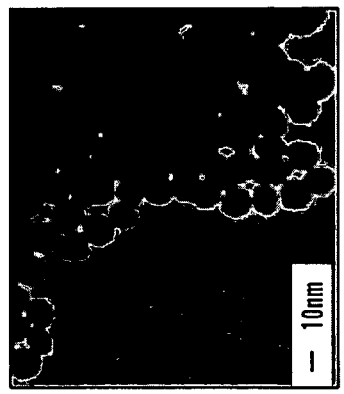
Figure 21B:
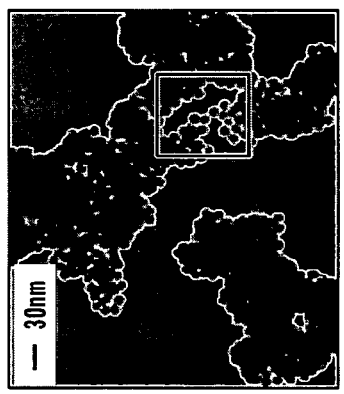
Figure 21E:
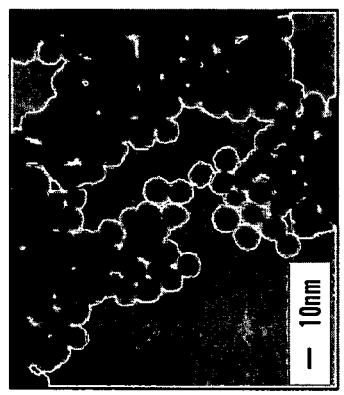
Figure 21A:
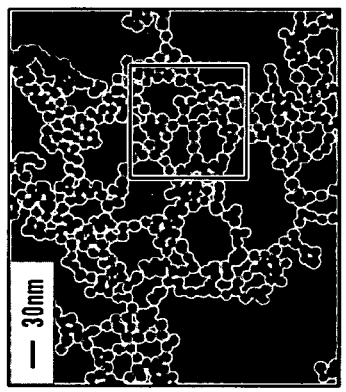
Figure 21D:
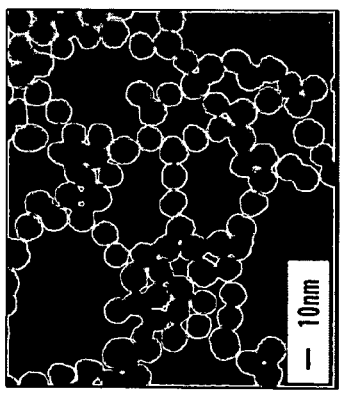

Upon completion of ICD-nanoparticle assembly reaction as reflected by the leveling off of the spectral evolution, the solution was briefly sonicated and samples were taken from the solution and examined using TEM. FIGS. 21 B and C show a representative set of TEM images for ICD-mediated assembly of $Au_{nm}$ derived from different concentrations of ICDs. The TEM image for $Au_{nm}$ in the absence of ICD (FIG. 21A) is included for comparison. In contrast to the fractal or chain-like features for $Au_{nm}$ solution in the absence of ICD (FIG. 21A), the samples taken from the solutions after adding ICD reveal features of highly-clustered nanoparticles (FIGS. 21B and 21C). Domains of the clusters with ~50 (FIG. 21B) and ~800 nm (FIG. 21C) have been observed by varying ICD concentrations, 0.16 (FIG. 21B) and 0.31 µM (FIG. 21C), respectively. The presence of individual nanoparticles along the edges of the larger clusters and the absence of free nanoparticles are indicative of the formation of assemblies of nanoparticles with an effective interparticle linkage. The size of the cluster and the 3D packing of particles in the cluster showed an apparent increase with the increase of ICD concentration.

Figure 22A:
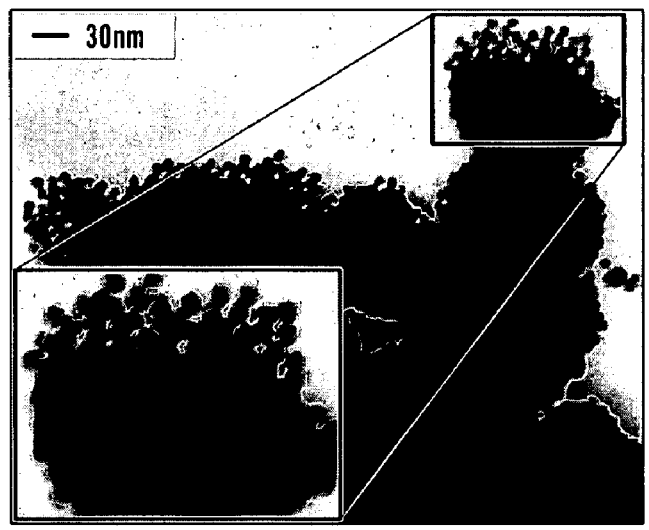
FIGS. 22A-B show TEM images of ICD-mediated assembly. The image of FIG. 22A is with [$Au_{nm}$]=7.9 nM and [ICD]=0.31 μM (r~39), where the image insert is a magnified view.
Figure 22B:
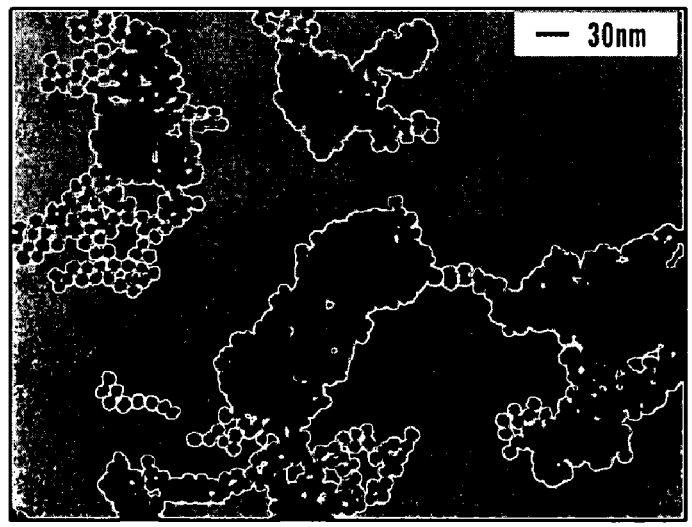

The clustering morphological features are further evidenced by a sample taken from the solution of ICD-mediated-assembly of $Au_{nm}$ with a higher $Au_{nm}$ concentration (with slightly different core size (~10.6 nm core size)) (FIG. 22A). In this case, the dye-mediated assembly exhibits spherically-shaped clusters of nanoparticles. A close examination of the clustered nanoparticles reveals the presence of certain interparticle ordering, as evidenced by the features along the edge of the clusters. Additional fine morphological features have also been observed by varying the concentration of nanoparticles. FIG. 22B shows another representative set of TEM images for ICD-mediated assembly of $Au_{nm}$ under the conditions corresponding to the spectral evolution shown in FIG. 20C. Because of the relatively-low concentration of ICD, the assemblies were soluble for weeks before precipitation occurred. From the ordered domains of nanoparticles around the large clusters or in the smaller clusters, the interparticle edge-to-edge distance was found to display an average value of 1.8±0.5 nm, which is larger than that found for citrate-capped $Au_{nm}$ particles (~1.3 nm). The increased interparticle distance reflects the presence of CWD molecules between the nanoparticles. Structurally, the long dimension of ICD molecule is 2.5 nm, whereas the width and thickness dimensions are ~1.5 and ~0.5 nm. The usual distance for π-π interactions is ~0.4 nm. By comparing these values with the interparticle distance measured (1.8 nm), two conclusions can be drawn. First, the nanoparticles in the assembly are individually isolated, which is consistent with the picture of molecular bridging between the nanoparticles as revealed by the adsorption data, and in contrast to those known for simple salt-induced aggregation of nanoparticles in which the nanoparticles are usually fused together because of the collapse of electrical double layers. Secondly, the dye molecules are likely oriented so that π-π interaction along the thicknesses dimension of the dye is responsible for bridging the neighboring nanoparticles.

FTIR characterizations of the nanoparticle assemblies were performed to assess the interparticle structural properties. The results for ICD-mediated assembly of $Au_{nm}$ revealed some similarities and differences in comparison with the spectral features for ICD and $Au_{nm}$. For example, the band detected for the asymmetric stretching mode of carboxylate seemed to be strong and clearly shifted to 1633 $cm^{-1}$. One possible explanation is the strong interaction between the carboxylate and the positively charged ammonium moiety of ICD, in contrast to the weak interaction with its counter ion ($Ma^+$). The band observed at 1460 $cm^{-1}$ could be due to symmetric stretching mode of carboxylate, mixed with some CH banding component from methylene groups. The band observed around 1378 $cm^{-1}$ could be assigned to part of the CH bending modes on the aromatic ring. Overall, features corresponding to the citrate molecules are predominant, whereas features from the dye molecules do not appear to be significant in terms of absorbance. Two possible scenarios include (1) the presence of a relatively small fraction of dye in the assembly in comparison with the capping citrate molecules, and (2) the strong π-π interaction of the aromatic rings influencing some of the vibrational properties. While an in-depth understanding of these two scenarios (e.g., using Raman spectroscopy) is part of on-going work, the fluorescence quenching data as presented in the next section provided important information for assessing the adsorption of dye molecules on the nanoparticles.

Example 11

Fluorescence Quenching Properties

Figure 23:
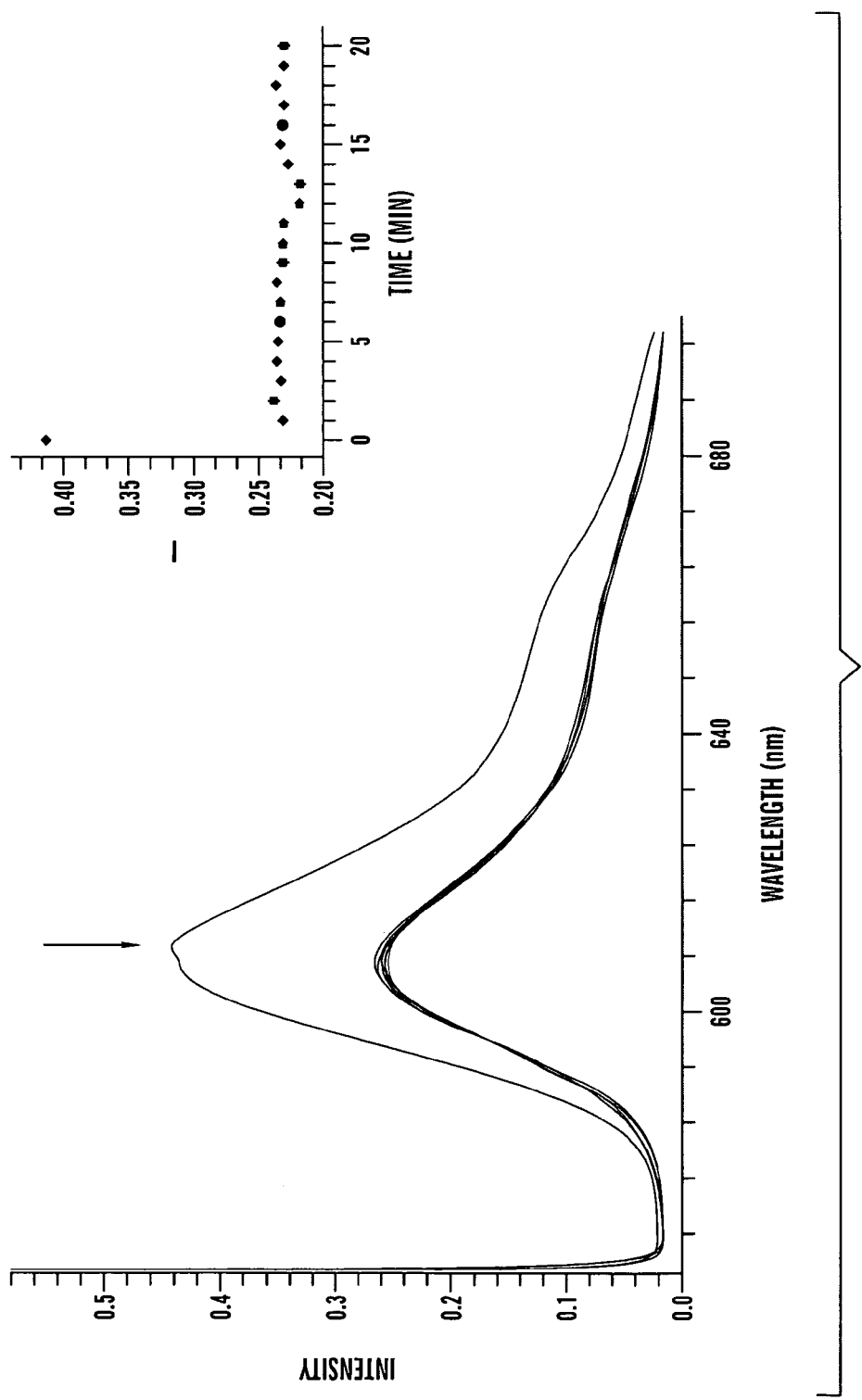
FIG. 23 shows florescence spectra of ICD upon addition of $Au_{nm}$. [$Au_{nm}$]=0.32 nM, [ICD]=1.0 μM. Each spectrum was taken with an increment of 1 min over a time length of 20 mins. The insert is a plot of intensity (I) at 608 nm vs. time. The arrow indicates the direction of the spectral evolution.

While ICD is highly fluorescent, the ICD-$Au_{nm}$ assembly was found to display fluorescence quenching properties, which provided an important means for assessing the mechanistic details of the interparticle interactions for the nanoparticle assembly. FIG. 23 shows a representative set of fluorescence spectral change for a solution of ICD upon addition of $Au_{nm}$. An important finding in this experiment is that the fluorescence quenching of ICD occurs almost immediately (<1 min), which is in contrast to the gradual UV-Vis spectral evolution for the dye-mediated assembly of nanoparticles. The rapid quenching is suggestive of a rapid adsorption of ICDs on $Au_{nm}$, whereas the slow calorimetric change reflects the slower interparticle ligand interaction following the ligand adsorption. The quenching is due to energy transfer as a result of the adsorption of ICD on $Au_{nm}$. Previous studies have shown that the fluorescence quenching is dependent on the distance between dye and metal particle surface. Quenching usually occurs at a distance of a few nm (<~5 nm) by Foester energy transfer from the fluorophore to the surface plasmon resonance absorption of the metal particles. See Dulkeith, E., et al., Nano Lett. 5: 585 (2005), which is hereby incorporated by reference in its entirety. In the present case, the distance between $Au_{nm}$ and ICD is defined by a combination of the electrostatic and π-π interactions between the negative citrate and the positive cyanine groups, which is approximately 1.8 nm and falls in the range known for fluorescence quenching.

Figure 24:
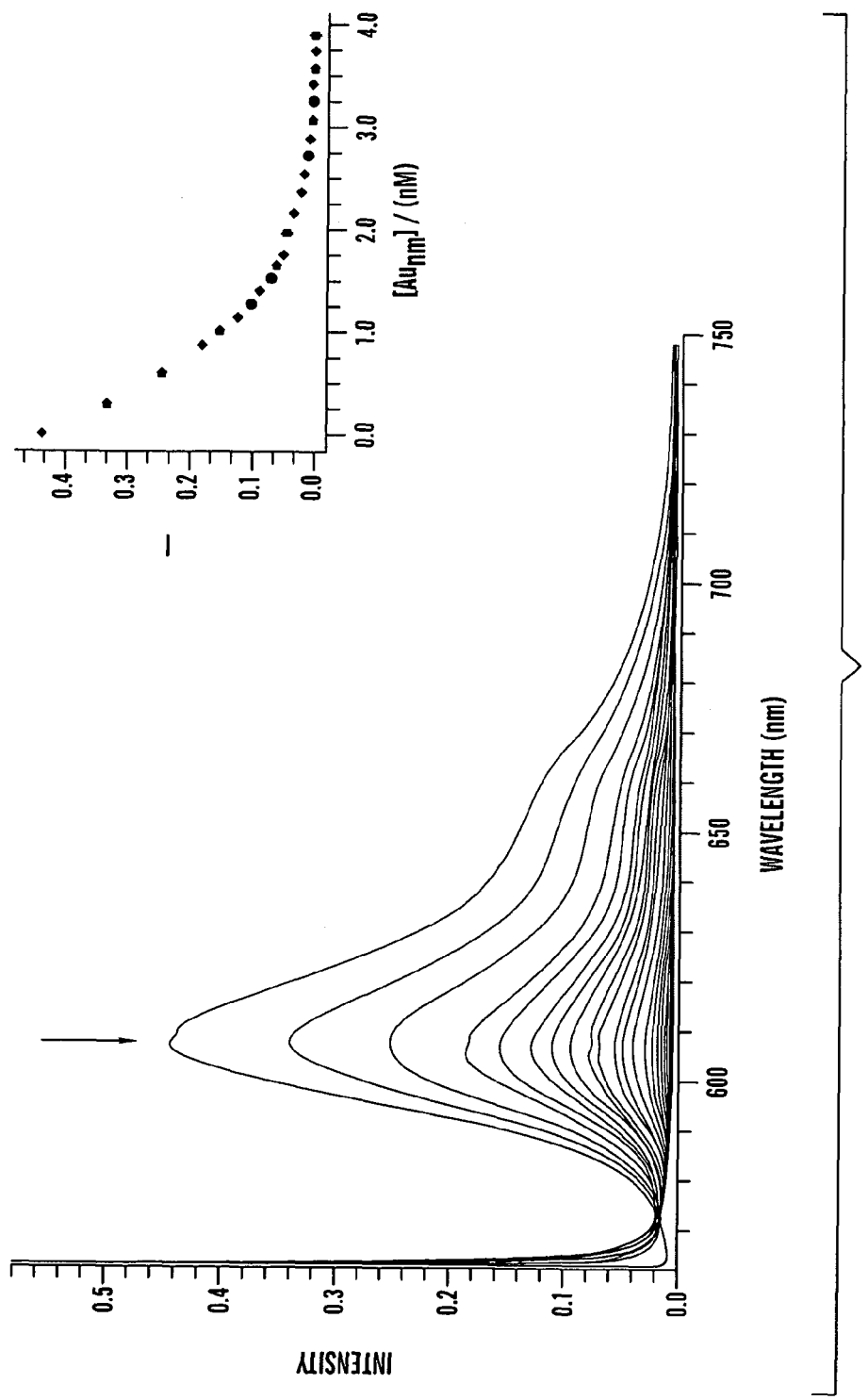
FIG. 24 shows fluorescence spectra of ICD (initial concentration: 1 μM) upon addition of $Au_{nm}$ (12.6 nM) with an increment of either 25 or 50 μL. Each spectrum was recorded 5 min after the addition of $Au_{nm}$. The insert is a plot of the intensity (I) at 606 nm vs. concentration of $Au_{nm}$. The arrow indicates the direction of the spectral evolution.

The fluorescence quenching is found to be quantitatively related to the adsorption of dye on $Au_{nm}$. FIG. 24 shows a representative set of fluorescence data obtained by incrementally adding $Au_{nm}$ solution into the ICD solution. In this experiment, the total moles of ICD ($2 \times 10^{-9}$ moles) were kept constant while its concentration was diluted (1.45×) by the added volumes of $Au_{nm}$. The dependence of fluorescence quenching on the quantity of $Au_{nm}$ is clearly evidenced by the decrease of the fluorescence intensity as a function of the amount of $Au_{nm}$. This type of dependence is also reminiscent of quantitative titration of dye molecules by $Au_{nm}$. Assuming that the quenching only occurs for those ICDs that have direct interaction with $Au_{nm}$ surface, the maximum of the quenched ICDs are then restricted to a full monolayer coverage of ICD on the nanoparticle surface, which depends on the orientation of the adsorbed ICD. A lower limit coverage would be for a flat orientation of ICD adsorbing on the surface, whereas an upper limit value would be for a vertical adsorbing orientation. A simple model calculation in which ICD is approximated as a rectangular box with a dimension of 25 Å×15 Å×5.2 Å indicates that one $Au_{nm}$ (10.6 nm) can accommodate ~95 (for flat orientation) or ~270 (for vertical orientation along long-side) ICD molecules for a full monolayer coverage. For $1.2 \times 10^{15}$ dye molecules (the starting quantity), $1.3 \times 10^{13}$ (for flat orientation) or $4.4 \times 10^{12}$ (for vertical orientation along long-side) of $Au_{nm}$ would be needed in terms of forming a full monolayer coverage. In FIG. 24, the end point of the titration curve shows that $6.8 \times 10^{12}$ of $Au_{nm}$ were required to observe the complete quenching. The experimental result is remarkable by the fact that the end point falls in between the two calculated values ($1.3 \times 10^{13}$ and $4.4 \times 10^{12}$), suggesting the likelihood of a tilt orientation of dye molecules on the nanocrystal surface.

Figure 25:
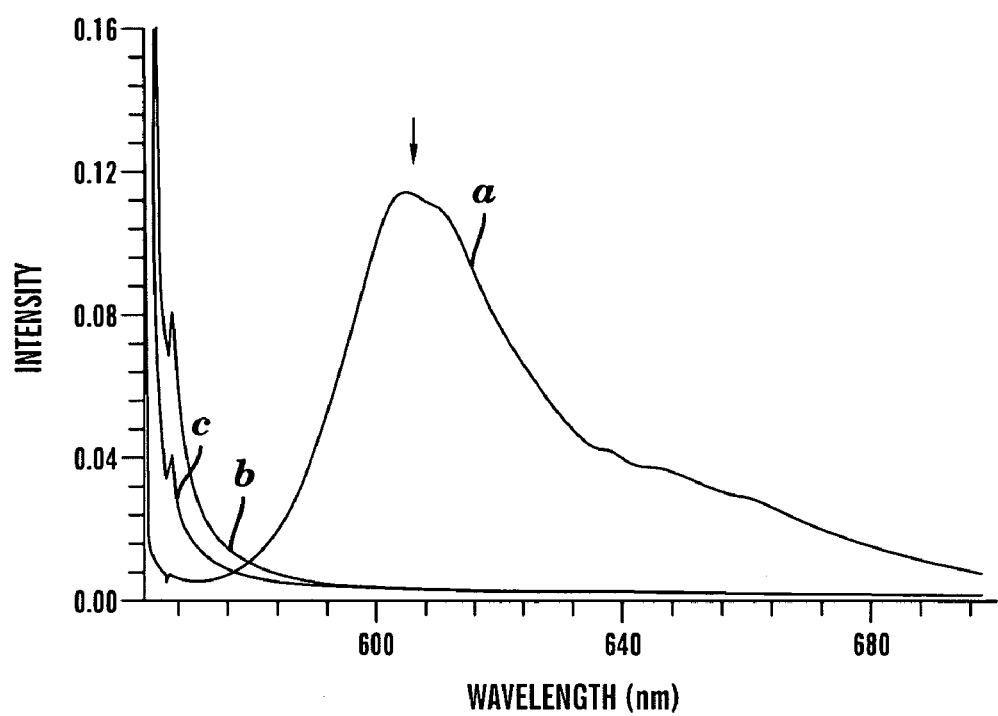
FIG. 25 shows fluorescence spectra showing quenching efficiency using $Au_{nm}$ of different concentrations ([$Au_{nm}$]=0 (a), 3.9 (b), 7.8 nM (c)), [ICD]=0.67 μM. The arrow indicates the direction of the spectral evolution.

The quantitative aspect for the fluorescence quenching is further examined by measurements with $Au_{nm}$ of a slightly-larger size (11.5 nm). Theoretically, the surface of one $Au_{nm}$ would accommodate ~110 ICDs (in flat orientation). For a solution of $1.2 \times 10^{15}$ ICD molecules (0.67 µM), a theoretical 100% quenching would require $1.1 \times 10^{13}$ $Au_{nm}$. FIG. 25 shows a set of data obtained according to this experimental design. Indeed, the addition of $7.1 \times 10^{12}$ $Au_{nm}$ to the solution of $1.2 \times 10^{15}$ ICD molecules was show to be sufficient to exhibit 100% quenching, corresponding to ~170 ICD quenchers per nanoparticle.

The above observation suggests that dye molecules are unlikely to adsorb horizontally on the nanocrystal surface (~110 dye/$Au_{nm}$). If the dye molecule is adsorbed vertically, ~320 dye molecules are required for a full monolayer coverage on a nanoparticle. The comparison between experimental data and theoretical estimates further demonstrate the likelihood of a tilt orientation for the adsorption of ICDs on the particle surface. As reflected by the calculation results from the experimental data, the observation of the slightly-slower quenching rate in the lower-concentration case is suggestive of the possibility of a more horizontal orientation of the dye molecule on the surface.

Figure 26A:
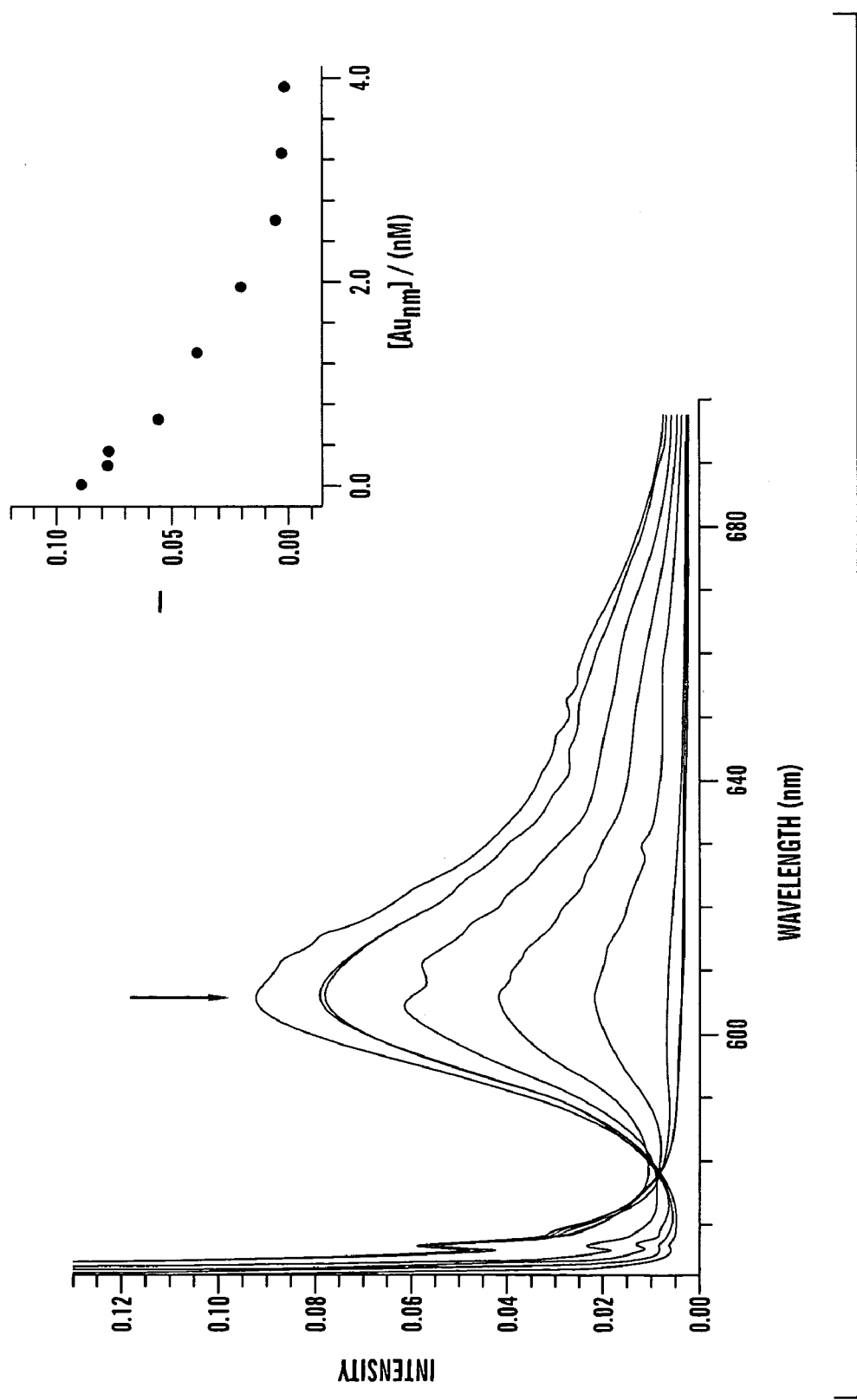
FIG. 26A shows the fluorescence spectra of ICD (0.67 μM) upon addition of $Au_{nm}$ (19.5 nM). Each spectrum was recorded 5 min after the addition of $Au_{nm}$. The insert is a plot of the intensity (I) at 608 nm vs. concentration of $Au_{nm}$. The arrow indicates the direction of the spectral evolution with nanoparticle concentration.
Figure 26B:
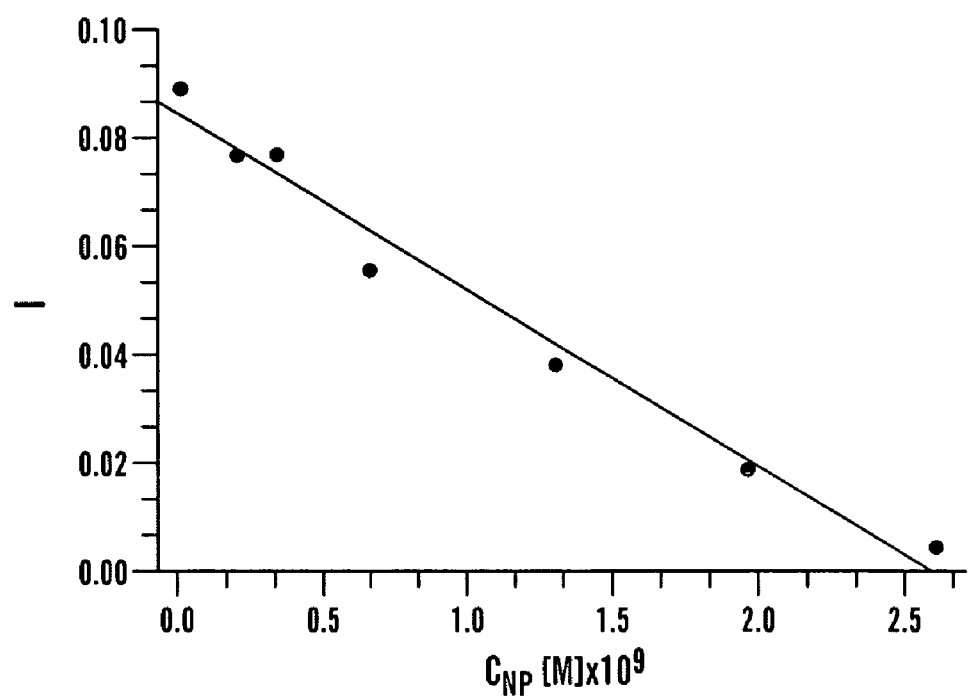
FIG. 26B shows a graph plotting the measured fluorescence intensity (I) at 608 nm vs. concentration of $Au_{nm}$ (linear regression; y=−3.20×10$^7$ x+0.083).

As shown in FIG. 26A, the fluorescence quenching is further analyzed as a function of $Au_{nm}$ concentration. This set of data was analyzed in two quantitative ways. First, the quenching efficiencies were compared between the calculated and experimental data (see Table 3).

TABLE 3

Table 3. Analysis of the fluorescence quenching data for a 0.67 μM solution of dye ($1.2 \times 10^{15}$ ICD) upon addition of different quantities of $Au_{nm}$.

| Fluorescence Intensity (608 nm)[a] | # of Au particles | % of dyes being quenched by Au (Exptl.)[b] | % of dyes being quenched by Au (Cal'd.)[c] |
|---|---|---|---|
| 0.089 | 0 | 0 | 0 |
| 0.077 | $3.5 \times 10^{11}$ | 13.4 | 5.8 |
| 0.077 | $5.9 \times 10^{11}$ | 13.7 | 9.6 |
| 0.055 | $1.2 \times 10^{12}$ | 37.5 | 19.5 |
| 0.038 | $2.4 \times 10^{12}$ | 56.9 | 38.3 |
| 0.019 | $3.5 \times 10^{12}$ | 78. | 58.3 |
| 0.005 | $4.7 \times 10^{12}$ | 94.5 | 78.2 |
| 0.002 | $5.9 \times 10^{12}$ | 97.6 | 97.6 |

[a]Baseline subtracted.
[b]Based on the change in fluorescence intensity upon addition $Au_{nm}$.
[c]The model calculation assumes that 1 $Au_{nm}$ can adsorb 200 dye molecules for a full monolayer coverage.

The calculation assumes that the surface of one $Au_{nm}$ nanocrystal can on average accommodate ~200 ICDs by considering an average of flat- and vertical-orientations. In Table 3, the general trend for the calculated and experimental quenching efficiencies data is quite consistent. The calculated quenching efficiency is slightly smaller than the experimental ones. For example, the addition of $3.5 \times 10^{12}$ $Au_{nm}$, into the dye solution is expected to quench 58.3% of dyes in the theoretical calculation. The change in fluorescence intensity showed a quenching efficiency of 78%. Secondly, the fluorescence quenching of ICD was found to be linearly dependent on $Au_{nm}$ concentration before reaching the end point of titration (<3.0 nM). On the basis of the above experimental results, the adsorption of ICD on the surface of the nanoparticle ($Au_{nm}$) can be considered to involve electrostatic interaction between the negatively-charged carboxylates of citrates on $Au_{nm}$ and the positively-charged nitrogen moieties of ICD in an steady state equilibrium (eqn. 1), which is a much faster process than the assembly process.

$C_1$ and $\theta_1$ are used to stand for the concentration of ICD in the solution and the surface fractional coverage of ICD on the negatively-charged sites of $Au_{nm}$, respectively. $\theta = \Gamma_1/\Gamma_0$ where $\Gamma_1$ represents surface coverage (moles/cm²) of ICD and $\Gamma_0$ the maximum monolayer surface coverage, which was estimated to be $4.43 \times 10^{-11}$ moles/cm² for flat orientation or $1.33 \times 10^{-10}$ (vertical orientation along long-side) and $2.2 \times 10^{-10}$ moles/cm² (vertical orientation along short-side) for vertical orientation. $C_0$ represents the initial concentration ICD ($C_1 = C_0 - C_{ads}$). The equilibrium for eqn. 1 can be described by a Langmuir type isotherm, i.e., $$K = \frac{\theta_1}{(1-\theta_1)C_1} \qquad (2)$$

where K represents equilibrium constant. Since the particle-dye interaction is dominant for the fluorescence quenching phenomenon, the contribution of intermolecular interactions can be ignored. Considering the relationship between the change of ICDs in the solution and those adsorbed on the $Au_{nm}$ surface (the total surface area of the nanoparticles used=(# of $Au_{nm}$)×(surface area of one particle)=($N_0$ $C_{NP}$ V)($SA_{NP}$)), one has $N_0V(C_0-C_1)=N_0\theta_1\Gamma_0(N_0$ $C_{NP}$ V($SA_{NP}$), where $N_0$ is Avogadro's number, V is the total volume of the solution, and $C_{NP}$ is the concentration of $Au_{nm}$, thus, $$\theta_1 = \frac{(C_0 - C_1)}{\Gamma_0 C_{NP} SA_{NP} N_0} \qquad (3)$$

by solving this equation for C1 with the consideration that K is a very large number, $$C_1 = -(N_0\Gamma_0 SA_{NP})C_{NP} + (C_0 - 1/K) \qquad (4)$$

it shows that the concentration of the dye is a linear function of the concentration of the nanoparticles. By further considering the concentration dependence of fluorescence intensity being measured, $I=k'bC_1$, where $k'=2.3$ $\Phi P_0 \in$ (see J. R. Lakowicz, *Principles of Fluorescence Spectroscopy*, Kluwer Academic/Plenum Press, New York, 1999, Second Edition; Skoog, D. A., et al., *Principles of Instrumental Analysis*, Saunders College Pub., 1998, which are hereby incorporated by reference in their entirety), b=cell path length, $\Phi$=quantum yield, $P_0$=power of the incident light, and $\in$=molar absorptivity of dye, $$I = (-k'b\ N_0\Gamma_0 SA_{NP})C_{NP} + k'b(C_0-1/K) \qquad (5)$$

Eqn. 5 shows a linear relationship between I and $C_{NP}$ where the slope=$-k'b\ N_0\Gamma_0 SA_{NP}$ and the y-intercept=$k'b(C_0-1/K)$. As shown by FIG. 12B, this relationship fits quite well with the experimental data. Using the slope and intercept values obtained, and other parameters, $C_0=6.67\times10^{-7}$ M; $\Gamma_0=4.43\times10^{-11}$ moles/cm² (as described earlier) and $SA_{NP}=4.17\times10^{-12}$ cm², k'b was found to be $2.87\times10^5$ M⁻¹, and K to be $2.65\times10^6$ M⁻¹. The latter shows indeed a large magnitude for the equilibrium constant, consistent with the fact that the adsorption of ICDs on the nanoparticle surface is thermodynamically favorable.

The quantum yield ($\Phi$) is further estimated under the experimental condition based on the experimental data. Using tetraphenylporphyrin (TPP) dissolved in benzene ($3.45\times10^{-5}$ M) as a standard ($\lambda_{ex}$: 550 nm, $\lambda_{em}$: 608 nm, $\Phi$: 0.11, $\in$: $7.3\times10^3$ M⁻¹ cm⁻¹), $P_0$ (=23.5) was obtained from the measured peak intensity ($I_{658nm}$=1.492). The value of $\Phi$, based on $k'=2.3$ $\Phi P_0 \in$ was estimated to be 0.05. If the linear regression data for [$Au_{nm}$]<1.6 nM (slope=$-3.88\times10^7$) were used, the $\Phi$ value was found to be 0.06. In a separate measurement of TPP and ICD in the absence of nanoparticles under the same conditions, the peak intensity ($I_{610nm}$=2.935) for a dye solution of $2.66\times10^{-6}$ M yields a $\Phi$ value of 0.18, which is larger by a factor of ~3 than that determined in the presence of nanoparticles. This reflects the significant effect of dye-$Au_{nm}$ interactions. This effect was further examined under a higher initial concentration of dye, as shown in FIG. 24 ([ICD]=1 μM). There was a slight volume increase due to the increment addition of $Au_{nm}$ solution into the solution of ICD, but it can be corrected based on the linear dependence of intensity on concentration, the value of $\Phi$ was found to be 0.25, which is larger by a factor of ~1.5 than that obtained in the absence of nanoparticles ($\Phi$=0.16). The results of these estimates, while varying within the experimental error range, demonstrated the important role played by the ICD-$Au_{nm}$ interactions in the solution. The dependence of fluorescence quenching on particle size was also examined, which suggested that the fluorescence intensity decrease as the core size of $Au_{nm}$ increases.

In conclusion, a unique combination of nanoparticles and dyes for studying the interparticle interactions and reactivities has been demonstrated. The combination of the indolenine cyanine dyes and the gold nanoparticles is shown to form J-aggregate bridged assembly of nanoparticles, in addition to hydrophobic interparticle interactions and electrostatic dye-particle interactions. Such interparticle interactions and reactivities are studied by probing the absorption of J-aggregates and fluorescence from the dyes and the surface plasmon resonance from the nanoparticles. The J-aggregation of the dyes adsorbed on the nanoparticles is shown to play an important role in the mediated assembly of nanoparticles. The J-aggregation of the dyes adsorbed on the nanoparticles is shown to play an important role in the assembly of nanoparticles. The spectral evolution of the J-band of the dyes and the surface plasmon resonance band of the nanoparticles were found to be sensitive to the nature of the charge and the structure of the dyes. The fluorescence quenching for the dyes were shown to be quantitatively related to the surface coverage of the dyes on the nanocrystal surfaces. These findings have provided important information for assessing a two-step process involving a rapid adsorption of the dyes on the nanoparticles and a subsequent assembly of the nanoparticles involving a combination of interparticle J-aggregation and hydrophobic interactions of the adsorbed dyes. In view of the electrostatic nature for the adsorption of dyes and the weak molecular interactions for the interparticle J-aggregation, the optical or spectroscopic properties are expected to be tunable by molecules that regulate the electrostatic, hydrophobic and π-π interactions, or display specific recognition capabilities to the interaction sites. Based on recent experiences in using dynamic light scattering techniques to probe nanoparticle assemblies in solution, part of the on-going work is to address the issues related to hydrodynamic sizes of the nanoparticle assemblies in the dye-nanoparticle system. See Maye, M. M., et al., *J. Phys. Chem., B* 109: 2578 (2005), which is hereby incorporated by reference in its entirety.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method of forming aggregates of nanoparticles and dyes, said method comprising:
   providing nanoparticles of a transition metal, wherein the nanoparticles are capped with positive or negative capping groups;
   providing cyanine dye molecules, which can be cationic, anionic, or neutral cyanine dye molecules; and
   contacting the nanoparticles and the cyanine dye molecules under conditions effective to form aggregates of a plurality of the nanoparticles and a plurality of the dye molecules, wherein the nanoparticles and the cyanine dye molecules interact non-covalently.

2. The method of claim 1, wherein the transition metal is selected from the group consisting of copper, silver, gold, and mixtures thereof.

3. The method of claim 2, wherein the transition metal is gold.

4. The method of claim 1, wherein the cyanine dye is a cationic cyanine dye.

5. The method of claim 1, wherein the cyanine dye is a anionic cyanine dye.

6. The method of claim 1, wherein the cyanine dye is a neutral cyanine dye.

7. The method of claim 1, wherein the diameter of the nanoparticles is 1 to 100 nanometers.

8. The method of claim 1, wherein the aggregates are J-aggregates.

9. The method of claim 1, wherein the nanoparticles and dye molecules aggregate through an interaction selected from the group consisting of electrostatic interactions hydrophobic interaction, and π-π interaction.

10. The method of claim 1, wherein the capping groups are selected from the group consisting of acrylates, N,N-trimethyl(undecylmercapto)ammonium, tetrabutylammonium tetrafluoroborate, tetramethylammonium bromide, cetyltrimethylammonium bromide, citrates, polymethacrylate, ascorbic acid, DNA, 2-mercaptopropionic acid, 3-mercaptopropionic acid, 11-mercaptoundecanoic acid, 10-mercaptodecane-1-sulfonic acid, 16-mercaptohexadecanoic acid, diimide, N-(2-mercaptopropionyl)glycine (tiopronin), 2-mercaptoethanol, 4-mercapto-1-butanol, dodecyl sulfate, amino acids, homocysteine, homocystine, cysteine, cystine, and glutathione.

11. An aggregate of a plurality of nanoparticles of a transition metal, which are capped with a positive or negative capping group, and a plurality of cyanine dye molecules, which can be cationic, anionic or neutral cyanine dyes, wherein the nanoparticles and the cyanine dye molecules interact non-covalently.

12. The aggregate of claim 11, wherein the transition metal is selected from the group consisting of copper, silver, gold, and mixtures thereof.

13. The aggregate of claim 12, wherein the transition metal is gold.

14. The aggregate of claim 11, wherein the cyanine dye is a cationic cyanine dye.

15. The aggregate of claim 11, wherein the cyanine dye is a anionic cyanine dye.

16. The aggregate of claim 11, wherein the cyanine dye is a neutral cyanine dye.

17. The aggregate of claim 11, wherein the diameter of the nanoparticles is 1 to 100 nanometers.

18. The aggregate of claim 11, wherein the aggregates are J-aggregates.

19. The aggregate of claim 11, wherein the nanoparticles and dye molecules aggregate through an interaction selected from the group consisting of electrostatic interaction, hydrophobic interaction, and π-π interaction.

20. A method of assembling aggregates of gold nanoparticles, said method comprising:
   providing gold nanoparticles capped with positive or negative capping molecules;
   providing cyanine dye molecules, which can be cationic, anionic, or neutral cyanine dyes; and
   contacting the capped gold nanoparticles and the cyanine dye molecules under conditions effective to form aggregates of a plurality of the gold nanoparticles and a plurality of the cyanine dye molecules, wherein the cyanine dye molecules and the gold nanoparticles form J-aggregates and undergo hydrophobic interaction.

21. A method of detecting an analyte in a sample comprising:
- providing a sample potentially containing the analyte;
- providing the aggregate of claim 11;
- contacting the sample with the aggregate; and
- detecting a change in the aggregate caused by the analyte, whereby the detection of such a change permits detection of the analyte in the sample.

22. The method of claim 21, wherein said detecting comprises detecting a change by spectroscopy.

23. The method of claim 22, wherein the spectroscopy is selected from the group consisting of surface plasmon resonance spectroscopy, surface enhanced Raman scattering spectroscopy, fluorescence spectroscopy, and absorption spectroscopy.

* * * * *